(12) United States Patent
Debarros et al.

(10) Patent No.: US 12,036,411 B2
(45) Date of Patent: Jul. 16, 2024

(54) MEASUREMENT OF ELECTROPHYSIOLOGICAL SIGNALS DURING STIMULATION OF A TARGET AREA OF A BODY

(71) Applicant: Oxford University Innovation Limited, Oxford (GB)

(72) Inventors: Jean Debarros, Oxford (GB); Huiling Tan, Oxford (GB); Peter Brown, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 314 days.

(21) Appl. No.: 17/282,133

(22) PCT Filed: Oct. 2, 2019

(86) PCT No.: PCT/GB2019/052777
§ 371 (c)(1),
(2) Date: Apr. 1, 2021

(87) PCT Pub. No.: WO2020/070492
PCT Pub. Date: Apr. 9, 2020

(65) Prior Publication Data
US 2021/0370070 A1 Dec. 2, 2021

(30) Foreign Application Priority Data
Oct. 3, 2018 (GB) ..................................... 1816141

(51) Int. Cl.
*A61N 1/36* (2006.01)

(52) U.S. Cl.
CPC ....... *A61N 1/36139* (2013.01); *A61N 1/3606* (2013.01)

(58) Field of Classification Search
None
See application file for complete search history.

(56) References Cited

U.S. PATENT DOCUMENTS

| 9,248,280 B2 | 2/2016 | Moffitt et al. |
| 2007/0146189 A1 | 6/2007 | Wesselink et al. |

(Continued)

OTHER PUBLICATIONS

International Search Report and Written Opinion for WO 2020/070492 (PCT/GB2019/052777), dated Dec. 9, 2019, pp. 1-8.
(Continued)

*Primary Examiner* — Ankit D Tejani
(74) *Attorney, Agent, or Firm* — Thomas|Horstemeyer, LLP

(57) ABSTRACT

When generating a stimulation signal comprising stimulation pulses delivered to a target area of a human or animal body, an electrophysiological signal measured from the body for closed-loop control of the stimulation signal, is sampled, at a sampling frequency in an analogue-to-digital converter for deriving a feedback signal for closed-loop control of the stimulation signal. The generation of the stimulation signal and the sampling of the electrophysiological signal are synchronised and have a relative phase selected to cause the sampling to occur outside the stimulation pulses, which prevents the effect of the stimulation pulses from interfering with the digital electrophysiological signal, whiles allowing maintenance of Nyquist-Shannon rules and the integrity of the discrete Laplace transform (z-transform) required in discrete control theory.

23 Claims, 31 Drawing Sheets

(56) References Cited

U.S. PATENT DOCUMENTS

| | | | |
|---|---|---|---|
| 2008/0114417 | A1 | 5/2008 | Leyde |
| 2010/0331916 | A1 | 12/2010 | Parramon et al. |
| 2015/0119949 | A1 | 4/2015 | Tscherch et al. |
| 2018/0199841 | A1 | 7/2018 | Yang et al. |
| 2018/0303414 | A1* | 10/2018 | Toth ................ A61B 5/4848 |

OTHER PUBLICATIONS

UK Search Report for GB 1816141.4, dated Mar. 25, 2019, pp. 1-3.
Benabid, A. L., Pollak, P., Louveau, A., Henry, S., & Rougemont, J. de, (1987), 'Combined (thalamotomy and stimulation) stereotactic surgery of the vim thalamic nucleus for bilateral parkinson disease', Stereotactic and Functional Neurosurgery, vol. 50, No. 1-6, pp. 344-346.
Hariz, M., (2017), 'My 25 stimulating years with dbs in parkinson's disease', Journal of Parkinson's Disease, vol. 7, No. s1, pp. S33-S41.
Little, S., Pogosyan, A., Neal, S., Zavala, B., Zrinzo, L., Hariz, M., . . . Brown, P., (2013), 'Adaptive deep brain stimulation in advanced parkinson disease: adaptive dbs in pd', Annals of Neurology, vol. 74, No. 3, pp. 449-457.
Little, S., Beudel, M., Zrinzo, L., Foltynie, T., Limousin, P., Hariz, M., . . . Brown, P., (2015), 'Bilateral adaptive deep brain stimulation is effective in parkinson's disease', Journal of Neurology, Neurosurgery & Psychiatry, p. innp-2015-310972.
TMSi, (2017), 'Porti 7 user manual (revision 8)', TMSi, User manual 92-0207-0002-0-8.
Proakis, J. G. & Manolakis, D. G., (2002), 'Digital signal processing: principles, algorithms and applications'. New Delhi: Prentice-Hall of India, pp. 19-37.
TMSi, (2018), 'Porti 7 technical specifications (revision 5)', TMSi, User manual 92-0207-0002-0-8.
D'Antona, G. & Ferrero, A., (2006), 'Digital signal processing for measurement systems: theory and applications'. New York, NY: Springer, pp. 52-71.
Kent, A. R. & Grill, W. M., (2012), 'Recording evoked potentials during deep brain stimulation: development and validation of instrumentation to suppress the stimulus artefact', Journal of Neural Engineering, vol. 9, No. 3, p. 036004.
Rossi, L., Foffani, G., Marceglia, S., Bracchi, F., Barbieri, S., & Priori, A., (2007), 'An electronic device for artefact suppression in human local field potential recordings during deep brain stimulation', Journal of Neural Engineering, vol. 4, No. 2, p. 96.
Arlotti, M., Rossi, L., Rosa, M., Marceglia, S., & Priori, A., (2016), 'An external portable device for adaptive deep brain stimulation (adbs) clinical research in advanced parkinson's disease', Medical Engineering and Physics, vol. 38, No. 5, pp. 498-505.
Arlotti, M., Marceglia, S., Foffani, G., Volkmann, J., Lozano, A. M., Moro, E., Priori, A., (2018), 'Eight-hours adaptive deep brain stimulation in patients with parkinson disease', Neurology.
Steigerwald et al., 'Pulse duration settings in subthalamic stimulation for parkinson's disease', Movement Disorders, vol. 33, No. 1, pp. 165-169 (2018).
Cagnan, H., Pedrosa, D., Little, S., Pogosyan, A., Cheeran, B., Aziz, T., . . . Brown, P., (2017), 'Stimulating at the right time: phase-specific deep brain stimulation', Brain, vol. 140, No. 1, pp. 132-145.
Santillán-Guzmán, A., Heute, U., Muthuraman, M., Stephani, U., & Galka, A., (2013), 'DBS artifact suppression using a time-frequency domain filter', Conference proceedings: . . . Annual International Conference of the IEEE Engineering in Medicine and Biology Society. IEEE Engineering in Medicine and Biology Society. Annual Conference, vol. 2013, pp. 4815-4818.
Stanslaski, S., Afshar, P., Cong, P., Giftakis, J., Stypulkowski, P., Carlson, D., . . . Denison, T., (2012), 'Design and validation of a fully implantable, chronic, closed-loop neuromodulation device with concurrent sensing and stimulation', IEEE Transactions on Neural Systems and Rehabilitation Engineering, vol. 20, No. 4, pp. 410-421.
Zbrzeski, A., Lewis, N., Rummens, F., Jung, R., N'Kaoua, G., Benazzouz, A., & Renaud, S., (2013), 'Low-gain, low-noise integrated neuronal amplifier for implantable artifact-reduction recording system', Journal of Low Power Electronics and Applications, vol. 3, No. 3, pp. 279-299, Web: http://www.mdpi.com/2079-9268/3/3/279.
Hashimoto, T., Elder, C. M., & Vitek, J. L., (2002), 'A template subtraction method for stimulus artifact removal in high-frequency deep brain stimulation', Journal of Neuroscience Methods, vol. 113, No. 2, pp. 181-186.
Wagenaar, D. A. & Potter, S. M., (2002), 'Real-time multi-channel stimulus artifact suppression by local curve fitting', Journal of Neuroscience Methods, vol. 120, No. 2, pp. 113-120.
Al-Ani, T., Cazettes, F., Palfi, S., & Lefaucheur, J.-P., (2011), 'Automatic removal of high-amplitude stimulus artefact from neuronal signal recorded in the subthalamic nucleus', Journal of Neuroscience Methods, vol. 198, No. 1, pp. 135-146.
Sun, Y., Farzan, F., Garcia Dominguez, L., Barr, M. S., Giacobbe, P., Lozano, A. M., . . . Daskalakis, Z. J., (2014), 'A hovel method for removal of deep brain stimulation artifact from electroencephalography', Journal of Neuroscience Methods, vol. 237, pp. 33-40.
Qian, X., Chen, Y., Feng, Y., Ma, B., Hao, H., & Li, L., (2017), 'A method for removal of deep brain stimulation artifact from local field potentials', IEEE transactions on neural systems and rehabilitation engineering: a publication of the IEEE Engineering in Medicine and Biology Society, vol. 25, No. 12, pp. 2217-2226.
Blum, R. A., Ross, J. D., Brown, E. A., & DeWeerth, S. P., (2007), 'An integrated system for simultaneous, multichannel neuronal stimulation and recording', IEEE Transactions on Circuits and Systems I: Regular Papers, vol. 54, No. 12, pp. 2608-2618.
Brown, E. A., Ross, J. D., Blum, R. A., Nam, Y., Wheeler, B. C., & DeWeerth, S. P., (2008), 'Stimulus-artifact elimination in a multi-electrode system', IEEE Transactions on Biomedical Circuits and Systems, vol. 2, No. 1, pp. 10-21.
Rolston, J. D., (2009), 'A low-cost multielectrode system for data acquisition enabling real-time closed-loop processing with rapid recovery from stimulation artifacts', Frontiers in Neuroengineering, vol. 2, Web: http://journal.frontiersin.org/article/10.3389/neuro.16.012.2009/abstract.
Rolston, J. D., Gross, R. E., & Potter, S. M., (Sep. 2009), 'NeuroRighter: closed-loop multielectrode stimulation and recording for freely moving animals and cell cultures', pp. 6489-6492.
Unser, M., (2000), 'Sampling-50 years after shannon', Proceedings of the IEEE, vol. 88, No. 4, pp. 569-587.
Russo et al., 'Effective Relief of Pain and Associated Symptoms With Closed-Loop Spinal Cord Stimulation System: Preliminary Results of the Avalon Study', Neuromodulation. Jan. 2018;21(1):38-47. doi: 10.1111/ner.12684. Epub Sep. 18, 2017.
Kobayashi et al., 'Cardiac Autonomic Nerve Stimulation in the Treatment of Heart Failure', Ann Thorac Surg. Jul. 2013; 96(1): 339-345.
Zrenner et al., 'Closed-Loop Neuroscience and Non-Invasive Brain Stimulation: A Tale of Two Loops', Front Cell Neurosci. 2016; 10: 92.
Lio, G., Thobois, S., Ballanger, B., Lau, B., & Boulinguez, P., (2018), 'Removing deep brain stimulation artifacts from the electroencephalogram: issues, recommendations and an open-source toolbox', Clinical Neurophysiology, vol. 129, No. 10, pp. 2170.

* cited by examiner

Fig. 5
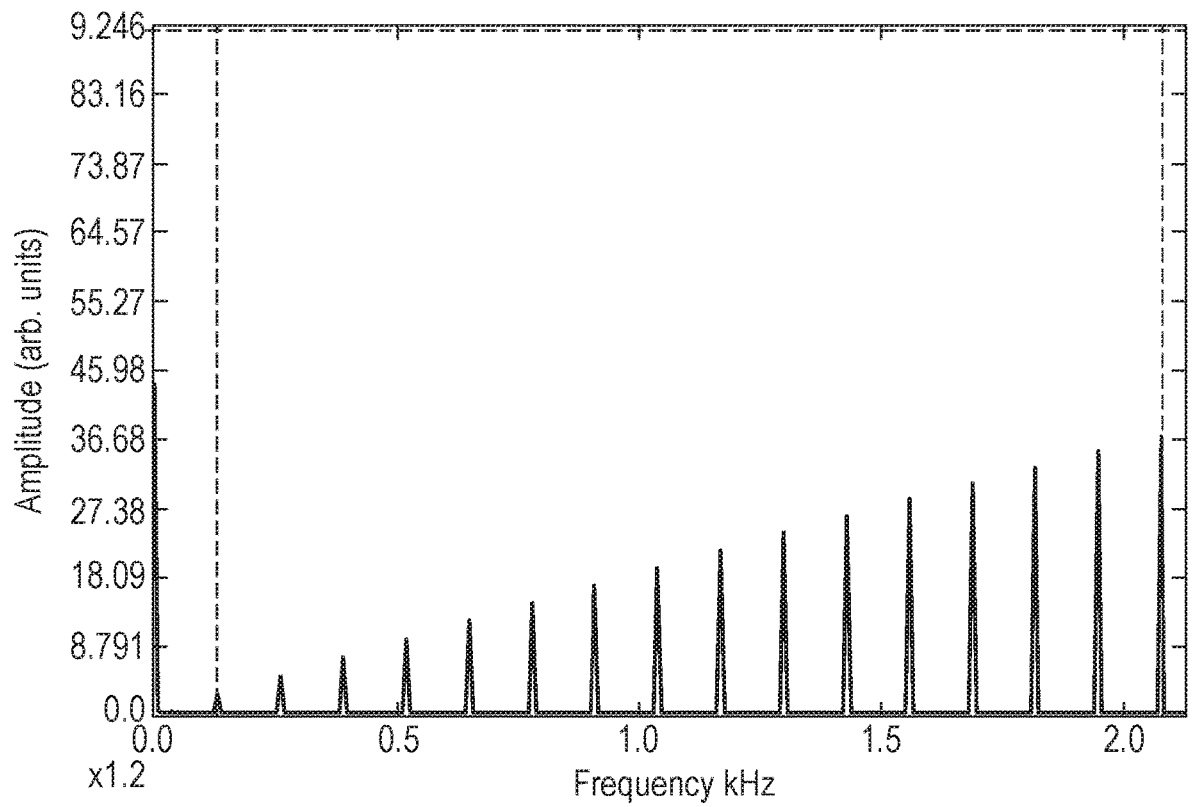
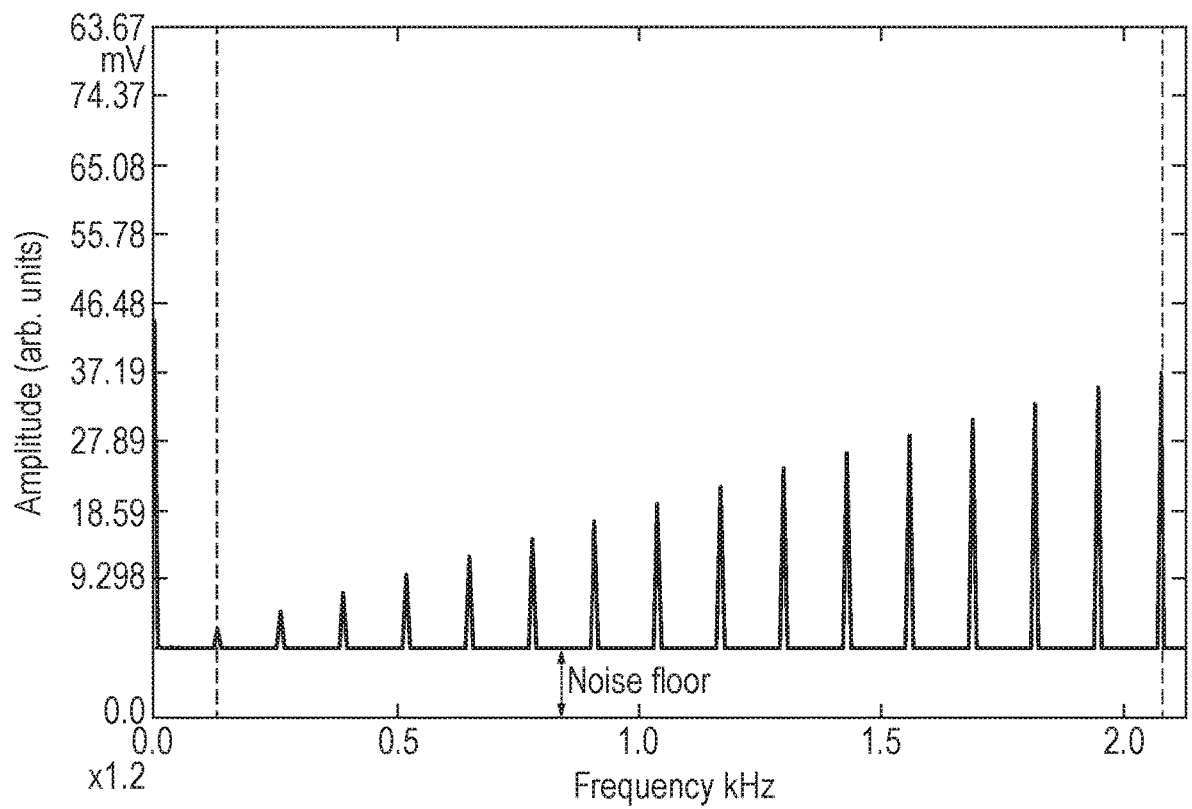

MEASUREMENT OF ELECTROPHYSIOLOGICAL SIGNALS DURING STIMULATION OF A TARGET AREA OF A BODY

CROSS-REFERENCE TO RELATED APPLICATIONS

This application is the National Stage of International Application No. PCT/GB2019/052777, filed Oct. 2, 2019, which claims priority to GB 1816141.4, filed Oct. 3, 2018, which are entirely incorporated herein by reference.

The present invention relates to measurement of an electrophysiological signal from a human or animal body for closed-loop control of a stimulation signal applied to a target area of the body.

Examples of scenarios where such closed-loop stimulation may be performed include (but are not limited to) adaptive Deep Brain Stimulation (aDBS), closed-loop spinal cord stimulation, peripheral or autonomic nerve stimulation, and closed-loop non-invasive brain stimulation.

By way of example, deep brain stimulation (DBS) will be considered. DBS was first introduced in 1987 by Benabid, Pollak et al. (Reference 1) and now represents a standard surgical procedure used worldwide to alleviate symptoms in different movement disorders such as Parkinson's disease (PD), essential tremor and dystonia (Reference 2). DBS has also been proposed and tested for the treatment of psychiatric disorders such as major depression, obsessive compulsive disorder (OCD), addiction and eating disorders. Currently available DBS devices deliver electrical pulses to the target brain area continuously at a constant frequency of usually 130 Hz and fixed amplitude. This is often referred to as 'continuous DBS' (cDBS). Although cDBS already confers major therapeutic benefits, especially in movement disorders, there is vast scope for improvement since cDBS is power inefficient, can induce side effects such as dysarthria, and lead to a reduction of efficacy due to 'habituation' of brain circuits to the stimulation (Reference 2).

Therefore, much of the current research and development focuses on selective delivery of the stimulation signal when it is required. This approach relies on recording and interpreting the electrophysiological signal measured close to the stimulation site in real-time to extract relevant information, and control the stimulation signal delivered to the target area. This is referred to as closed-loop DBS or 'adaptive DBS' (aDBS). The proof-of-concept and clinical benefits of aDBS have been demonstrated (References 3 and 4).

Closed-loop DBS has shown great potential in reducing side effect in people with Parkinson's disease (PD); and closed-loop approaches are receiving increasing attention in other fields such as deep brain stimulation for psychiatric disorders, spinal cord stimulation, peripheral or autonomic nerve stimulation and non-invasive brain stimulation. However, this new approach suffers from an important technological limitation that the electrophysiological signal measured close to the stimulation target as a feedback signal is corrupted by large electrical artefacts derived from the stimulation signal. This is an inevitable consequence of the electrical stimuli delivered simultaneously during recording. This leads to significant problems. A voltage artefact is superposed on the electrophysiological signal when the electrophysiological signal is sampled at a relatively high frequency. The voltage artefact is extremely large, typically of the order of a million times the level of the electrophysiological signal. Similarly, a low signal to noise ratio (SNR), i.e. high noise floor, arises due to aliasing when the electrophysiological signal is sampled at the relatively low frequency normally used in practical closed-loop DBS applications.

These problems corrupt the extracted LFP signal and making it less suitable for closed-loop applications. Both the high superposed voltage artefact and the elevated noise floor (leading to a low signal-to-noise ratio), represent important challenges to closed-loop DBS because of the resultant amplitude of measured signal is significantly distorted, highly variable, and information extracted from these signals would be suboptimal when implementing closed-loop control of stimulation.

Over the last two decades, several authors have proposed a range of solutions that can be classified in three categories; namely filtering, template removal and 'blanking', as follows.

The filtering approaches are as follows.

Rossi et al. proposed a system that may be referred to as the "FilterDBS" based on a 10th order low-pass filter completed by cascading five 2nd order classical Sallen-Key low-pass filters (Reference 10). They reported that FilterDBS has a gain of −100 dB at 130 Hz which is the frequency of the stimulation generator clock. A portable device for aDBS using this approach has recently been proposed (References 11 and 12). However, FilterDBS is limited to the spectrum band of 2-40 Hz (Reference 10). In addition, the 10th order filter introduces a large phase-shift, which limits the use of FilterDBS on applications requiring accurate estimation of the phase; like in phase-specific closed-loop DBS (Reference 14). Also, Little et al. compared continuous DBS (cDBS) to adaptive DBS (aDBS) using a 4th filter (References 3 and 4), which might not be sufficient to suppress the aliasing noise. More recently, Santillán-Guzmán et al. reported an offline method aiming at suppressing the DBS artefacts by means of iterative filtering until the quality was good enough by visual inspection (Reference 15), but such an approach is not applicable in real-time closed-loop DBS.

Recognising the broad spectrum of the stimulation artefact and practical design constraints of implantable DBS devices, Stanslaski et al. adopted a system-level approach to mitigate the saturation and aliasing occurring in concurrent stimulation and recording (Reference 16). They proposed to handle stimulation artefact in the context of a system-wide solution with modest but acceptable control performance, instead of overcoming stimulation interference during sensing. To this end, they implemented a first-order band-pass filter before amplification and analogue spectral analysis, then applied a third-order low-pass antialiasing filtering before performing the digital conversion (Reference 16). The filtering was combined with a careful selection of the stimulation parameters. Then, they performed a numerical analysis of the digitised data to further mitigate residual stimulation interference due to electrode/tissue impedance mismatch and component mismatch in the front-end filtering. However, despite their efforts, the artefact interferences were not completely removed. Also, the authors mentioned that, since their method has been designed in the frequency domain, it does not translate easily into the temporal domain (Reference 16).

And, Lio et al. (Reference 31), after conducting a thorough systematic review of the different filtering approaches in the literature, have brought together all these different techniques into a single filtering framework and toolbox. At first, they stress that the sources of aliasing are multiple: the stimulation pulses, the use of a non-linear to analogue converters like the Sigma-Delta ADC, sample clock jittering, periodic quantisation noise, the unavoidable difference of the resolution of difference devices used and their imperfect synchronisation. Thus, stimulation pulses will not be measured in the exact same way even if a high sampling rate is used. Those together will make aliased low-frequency components very difficult to predict (Reference 31).

At the frontend, they indeed suggest to use the classical analogue antialiasing filter to reduce frequency band of the recorded signal contaminated by stimulation artefacts, and oversampling at the ADC to improve the signal-to-noise ratio. After conversion, at the digital domain, they suggest to proceed with an offline zero-phase digital lowpass filter with a cut-off frequency below the stimulation frequency to further reduce the artefact by removing all artefact frequencies above the stimulation frequency; but at this stage, aliased frequencies below the cut-off frequency will still remain unchanged. To deal with these aliased low-frequencies, they suggest to apply frequency-domain filtering techniques since DBS-induced artefacts can be assumed to be stationary; i.e. their power spectrum and phase remain constant over time. In particular, the authors suggest the use of the Hampel filter, which can detect outliers in the spectrum of the LFP signal, which is then converted back into the time domain via the inverse FFT. They propose also the use of matched filters, automatic dictation of the DBS pulses is the time domain and etc; those techniques are implemented in their DBSFILT toolbox that is freely available.

Overall, the artefact filtering approaches have in common a recording topology based on cascading low gain second-order filters stages (Reference 17), in order to filter out the stimulation artefacts, and to extract the useful signal in this situation of extremely low SNR. But, large remaining stimulation artefacts and/or temporal distortions of the recorded signals have demanded for a better solution.

The template removal approaches are as follows.

Template removal is an extension of the filtering in the time domain. It is based on the idea that assuming the shape of the stimulation is known, one could "subtract" (filter) it from the recording in the temporal domain in order to recover the useful signal.

In 2002, Hashimoto et al. proposed an off-line procedure for removing the stimulus artefacts from recorded extraneuronal single unit discharges during DBS (Reference 18). Their procedure consisted of estimating an artefact template, and then subtracting it from the original recorded signal. Although they reported their system removed the majority of stimulation artefact, this technique is not feasible in real-time applications such as closed-loop DBS.

At around the same time, Wagenaar and Potter proposed an approach based on local curve fitting to suppress artefact for real-time multi-channel recordings (Reference 19). The algorithm, called SALPA, despite being effective, requires a powerful computer to execute; this is incompatible with a low-computing power of embedded system. In addition, this technique assumes invariable artefact often violated in practice.

In 2012, Al-ani et al. introduced an on-line stimulus artefact template extraction combined with the ensemble empirical mode decomposition (EEMD), to automatically detect and remove artefact induced by stimulation (Reference 20). Sun et al. introduced a method based on matched-filters (Reference 21), further improved using a moving average subtraction (MAS) algorithm, together with a resampling technique for more accurate reconstruction of the artefact template. More recently, Qian et al. have proposed a template removal approach by rebuilding at each sample time the stimulation artefact template from the detrended raw LFP data before completing the final part of the digital conversion (Reference 22).

In summary, all these template removal techniques require an estimation of the template of the artefact in real-time, which is a very challenging technical problem, since the artefact signal as measured inside the brain is complex and potentially variable over time. These techniques also require to amplify the raw LFP with all the issues of saturation and resolution required to measure accurately LFP signals with an order of magnitude of $\mu V$. Together, any error in the template construction/reconstruction will lead to subtraction mismatch with the risk of generating more complex artefact patterns in return.

The blanking approaches are as follows.

Blum et al. proposed a multi-contact device that allows for arbitrary and independent configuration of individual contacts either for stimulation or recording (Reference 23). The artefact-elimination circuitry held the recording to its previous voltage during each stimulation pulse in order to minimise artefacts in the recorded LFP. But their solution needs about 2 ms to return to recording mode, which leads to a maximal sampling frequency of 500 Hz for an equivalent periodic and non-interrupted recording, as well potentially hindering the principles of discrete Laplace transform or z-Transform (not to be confused with the z Transform used in statistics to normalise a normally distributed random variable), which is at the heart of discrete closed-loop theory. Brown et al. proposed a similar technique based on a different electronic circuitry (Reference 24). Their solution improved the recording recovery time to 0.5 ms for adjacent contacts, but 3 ms otherwise. Later, Roston et al. proposed a relatively cost-effective solution, with a recording recovery time of less than 1 ms (References 25 and 26).

More recently, Kent and Grill have proposed an electronic circuitry to measure the evoked compound action potentials (ECAPs) elicited by the stimulation pulse (Reference 9). After careful characterisation of the sources of the stimulus artefact, they proposed their DBS-ECAP approach combining several cascaded low amplification and filtering stages, a circuitry that discharges the stimulating electrode after each pulse, and clamps the artefact to a vale of ±0.7 V. By doing so, they were able to reduce the recording recovery time to 0.5 ms for pulse-width of 50 to 100 $\mu s$.

Together, blanking only during the stimulus pulse has proven to be a very good solution, achievable with simple electronics. The main drawback is the recording recovery time that hinders the maximum recording frequency, and the high synchronicity required by the discrete Laplace transform (or more commonly known as the z-Transform) central in discrete closed-loop control, where the validity of the discrete transfer functions (transfer functions expressed with the z-variable) require a precise and stable sampling frequency. However, while blanking stands out for its performance and simplicity and is a much better approach than filtering and template removal, blanking does not entirely solve the problem of electrical artefacts derived from the stimulation signal, which remains the main technical challenge for closed-loop DBS to become a standard in clinical applications.

As a first aspect of the present invention, a method is provided for simultaneously generating a stimulation signal comprising stimulation pulses for stimulation of a target area of a human or animal body and sampling an electrophysiological signal measured from the body for closed-loop control by the stimulation signal, at a sampling frequency, by an analogue-to-digital converter, wherein the generation of the stimulation signal and the sampling of the electrophysiological signal by the analogue-to-digital converter are synchronised and have a relative phase selected to cause the sampling to occur outside the stimulation pulses.

By synchronising the generation of the stimulation signal and the sampling of the electrophysiological signal, and also selecting the relative phase, the sampling is guarantee to consistently and systematically will occur naturally outside of the stimulation pulses, without the need of any additional intervention. As a result, the recorded electrophysiological signal is not affected by artefacts from the stimulation signal, because the electrophysiological signal is sampled at a time when the stimulation pulses do not occur. The synchronisation enables this condition to continue, as in the absence of synchronisation it is inevitable that the sampling periodically occurs at the time of the stimulation pulse, leading to aliasing in the manner described above. However, the relative phase also needs to be selected as otherwise the sampling may occur at the time of every stimulation pulse which would increase, rather than decrease, the effective artefact caused by the stimulation signal.

In contrast to the blanking approach described above, the present method does not have a measurement recovery time. The present method is therefore an elegant and yet efficient approach to achieve simultaneous stimulation and measurement and is part of an intelligent stimulation approach. The sampling frequency may be selected to comply with Shannon-Whittaker-Kotelnikov sampling theorem condition and maintains the integrity of the requirements of the discrete Laplace transform (known as the z-Transform) necessary for closed-loop stimulation to work as defined by discrete control theory.

Typically, the sampling frequency at which the electrophysiological signal is sampled is a plural integer value times the stimulation frequency at which the simulation pulses are generated. This enables the sampling rate to be selected to provide coverage of the full bandwidth of the electrophysiological signal without aliasing components, while maintaining the effect of avoiding artefacts from the stimulation signal.

Typically, the plural integer value is at least one. For example, if the stimulation frequency takes a typical value of 130 Hz, then a plural integer of four provides a sampling frequency of 520 Hz, providing sampling of a bandwidth up to 260 Hz.

The control of the generation of the stimulation signal and the sampling of the electrophysiological signal can be implemented either in hardware with simple electronics or in software with minimal or no electronics, for example allowing in some cases a full implementation at the software level, which is suitable for some applications.

By way of example, in one implementation, the method may be implemented by generating a master clock signal, and by deriving a sampling clock signal and a stimulation clock signal synchronously from the master clock signal with a relative delay introduced between the sampling clock signal and the stimulation clock signal to adjust their relative phase, for example using a simple delay element. The sampling may then happen at timings controlled by the sampling clock signal and the stimulation pulses may be delivered at timings controlled by the stimulation clock signal.

In the simplest case, the sampling clock signal is the master clock signal.

The stimulation clock signal may be derived by frequency dividing the master clock signal by a plural integer value, in order to provide a sampling frequency which is a plural integer value times the stimulation frequency.

The digital electrophysiological signal derived by the analogue-to-digital conversion may be used to derive a feedback signal used to perform closed-loop control of the stimulation signal.

The method may be implemented entirely in a stimulation device or may further comprise measuring the electrophysiological signal that is used in the method and/or applying the stimulation signal to the brain in order to treat the patient.

The stimulation signal may be a DBS stimulation signal for application to a target area of the brain of the human or animal body in aDBS. However, the method disclosed herein is equally applicable to other forms of stimulation of any part of the human or animal body.

For example, the method may be applied to neuroscience applications where the stimulation signal target area is in the brain or any other part of the nervous system. A few examples are: closed-loop deep-brain stimulation for movement disorders or psychiatric disorders, closed-loop spinal cord stimulation (as used for example in chronic pain management), closed-loop cortical stimulation (as used for example in seizure control), peripheral or autonomic nerve stimulation, or closed-loop non-invasive brain stimulation.

More generally, the method may be applied to bioengineering applications where the stimulation signal is applied to a target area in any part of the body, for example non-invasive stimulation.

According to a second aspect of the present invention, there is provided a stimulation device in which a method similar to the first aspect of the present invention is implemented.

To allow better understanding, an embodiment of the present invention will now be described by way of non-limitative example with reference to the accompanying drawings, in which:

FIG. 5 is a pair of graphs of the frequency spectrum of the electrophysiological signal in the absence and presence of the stimulation signal illustrating the elevated noise floor dur to aliasing;

Figure 1:
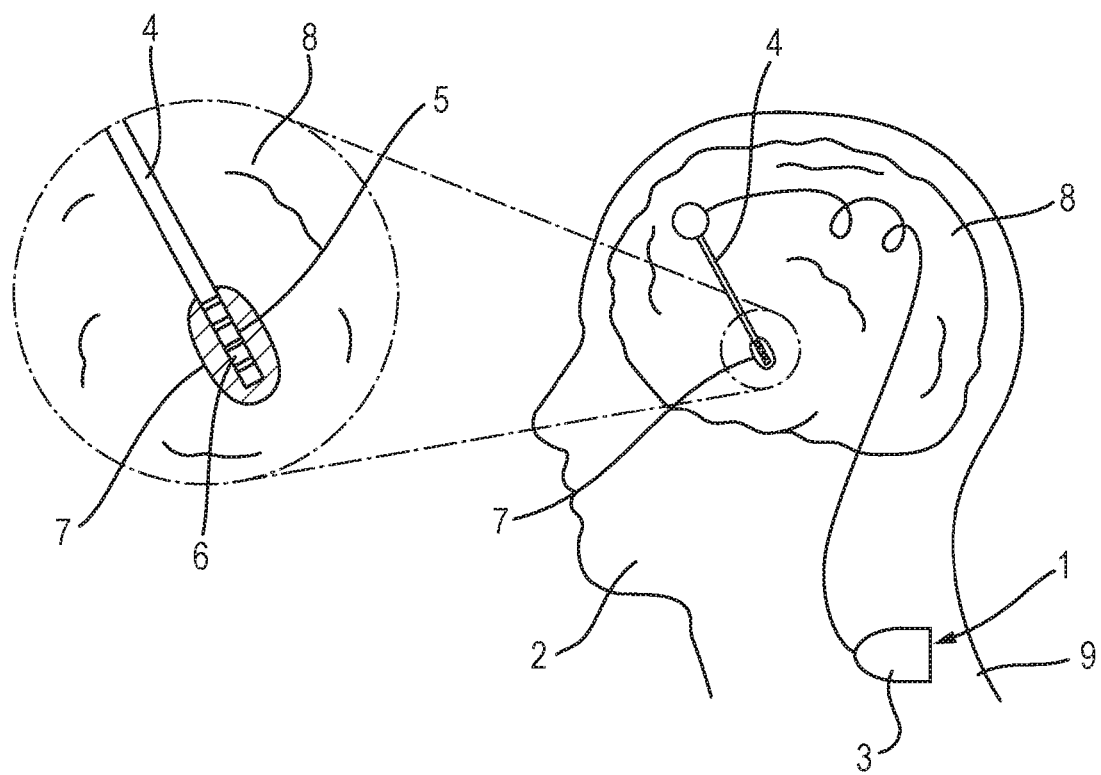
FIG. 1 is a pair of perspective views of a DBS device implanted in a patient.

There will first be described an example relating to aDBS. FIG. 1 shows a DBS device 1 implanted in a patient 2.

The DBS device 1 comprises a neurostimulator 3 which generates a stimulation signal comprising stimulation pulses and processes an electrophysiological signal as described in more detail below. The neurostimulator 3 is connected by a lead wire 4 providing parallel electrical connection to multiple electrodes 5 (four electrodes being shown by way of example) formed on the tip 6 of the lead wire 4.

The DBS device 1 is surgically implanted as follows. The tip 6 of the lead wire 4 is implanted into a target site 7 in the brain 8 of the patient 2 through a small opening in the skull of the patient. In this example, the target site 7 is the subthalamic nucleus (STN) for treatment of Parkinson's disease (PD), but in general the target site 7 could be another site in the brain 8 or elsewhere in the body (spinal cord, peripheral or autonomic nerves etc). The neurostimulator 3 is implanted into the thorax 9 of the patient 2 near the collarbone, with the lead wire 4 extending under the skin of the patient 2.

Figure 2:
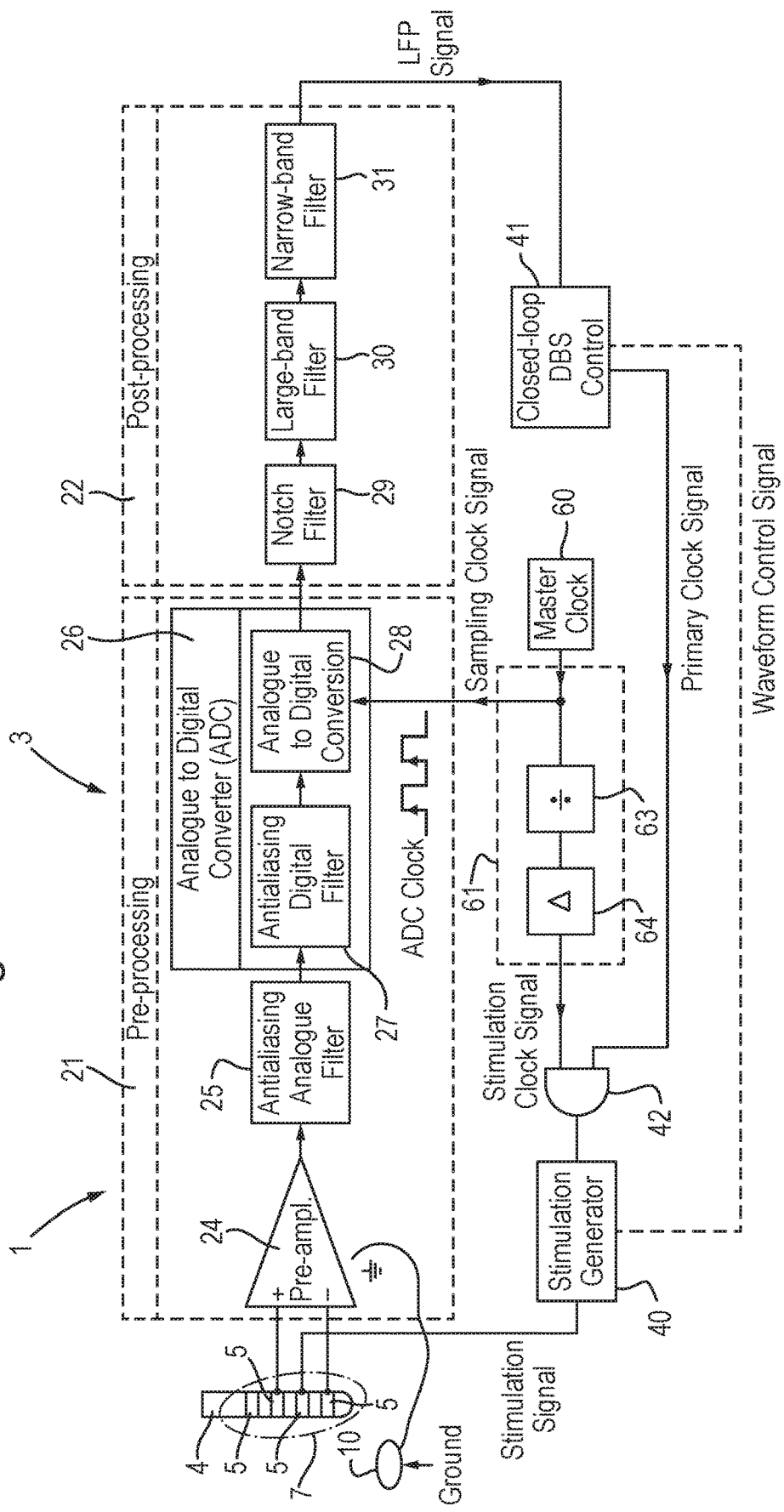
FIG. 2 is a diagram of the neurostimulator of the DBS device.

The neurostimulator 3 contains electronic components that are shown in FIG. 2, representing the overall structure of an intelligent deep brain stimulation (iDBS) closed-loop device, which will now be described. The neurostimulator 3 is provided with a ground 10 that is normally placed far away from the electrodes 5. When the overall DBS is internalised, the ground 10 may be connected to the case of the neurostimulator 3 implanted under the skin at the thoracic level, although during externalisation, e.g. for research purpose, the ground 10 may be taken from a part of the skin that minimises electrocardiogram (ECG) artefacts, usually the arm, neck or shoulder.

The neurostimulator 3 includes a stimulation generator 40 which generates an electrical stimulation signal comprising the stimulation pulses. The stimulation signal has a waveform for deep brain stimulation of the brain 8. The waveform may be selected to treat a disorder in the brain 8, including movement disorders, such as Parkinson's disease (PD), or other neurological and psychiatric disorders.

For treatment of PD, the stimulation signal may take a conventional form, for example as disclosed in References 1 and 2.

By way of example, the stimulation signal may comprise stimulation pulses having any or all of the following characteristics. The stimulation signal may comprise a pair of stimulation pulses of positive and negative polarity. The stimulation pulse may be of different shapes. The stimulation pulses may have periods in a range from a lower limit of 0.1 µs, preferably 1 µs, to an upper limit of 5000 ms, preferably 500 µs. For example, the period may typically be 60 µs. The stimulation pulses may have periods that are the same or different. The stimulation pulse pairs may have no separation or may have a separation. Where present, the separation may be less than 1000 µs, preferably less than 500 µs, typically 20 µs, and/or may be less than the duration of each of the pulses. The stimulation pulses may have an amplitude in a range from 0.1 V to 10.0 V. The stimulation signal may have a frequency in the range from 1 Hz to 500 Hz, typically being 130 Hz in currently available devices.

Figure 3:
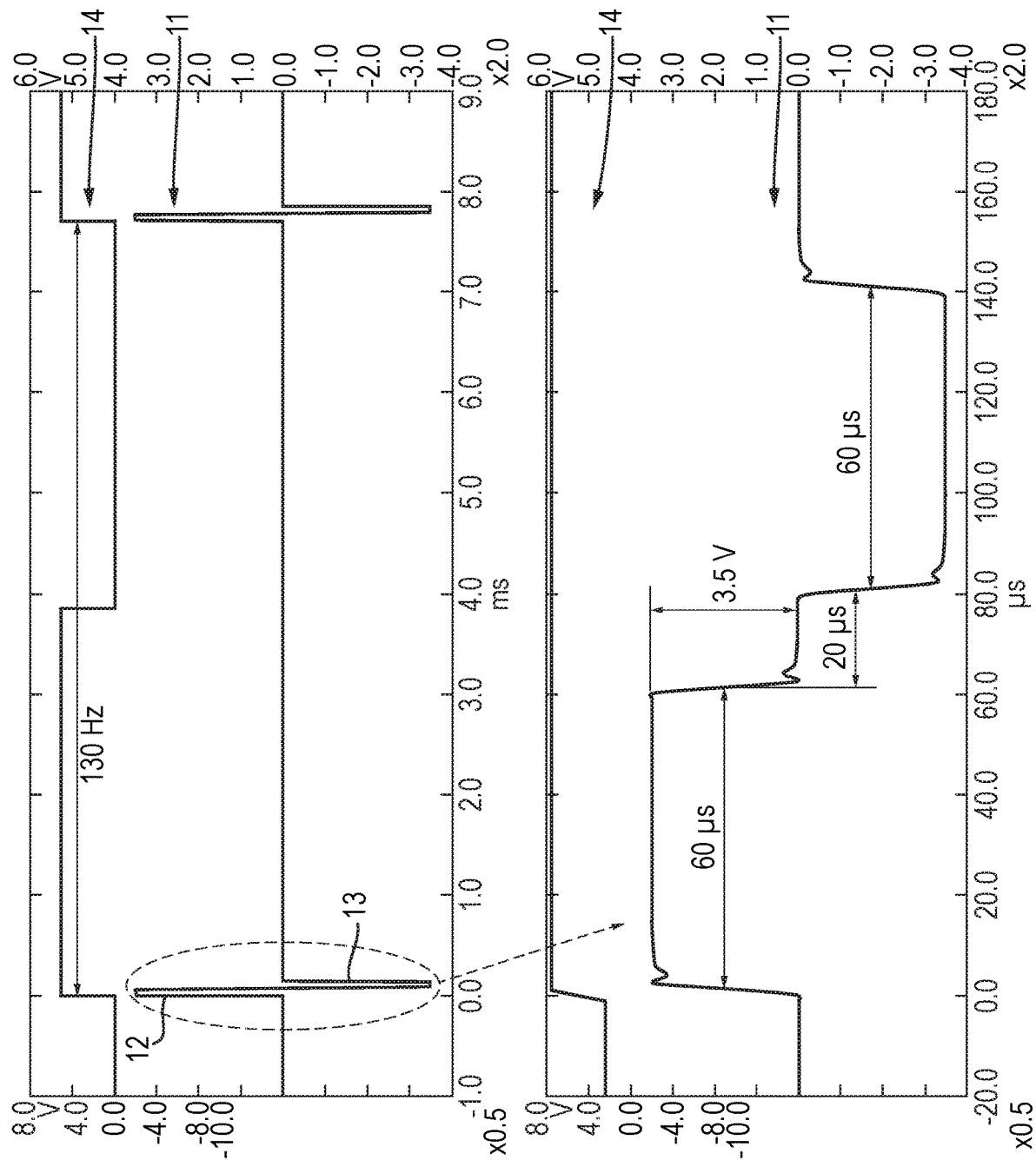
FIG. 3 is a pair of graphs of the same stimulation signal over two different time scales.

By way of example, FIG. 3 illustrates the temporal waveform of an example of a stimulation signal 11 at a stimulation frequency of 130 Hz. The stimulation signal 11 comprises a pair of stimulation pulses 12 and 13 of positive and negative polarity, respectively. The stimulation pulses 12 and 13 each have a length of 60 µs, and have a separation of 20 µs. The stimulation pulses 12 and 13 have a magnitude of 3.5 V. The stimulation pulses 12 and 13 occur at timings controlled by a stimulation clock 14 which drives the generation of the stimulation pulses 12 and 13. At every rising-edge of the stimulation clock, the first stimulation pulse 12 of the required duration is generated, then a delay by the amount of time representing the pulse gap is introduced before generating the second stimulation pulse 13.

The stimulation signal generated by the neurostimulator 3 is supplied to one of the electrodes 5a and thereby applied to the brain 8.

Whereas current clinical DBS devices deliver electrical stimulation pulses of the form shown in FIG. 3 to the target site continuously, i.e. cDBS, the neurostimulator 3 is configured to perform an intelligent closed-loop deep brain stimulation (iDBS) as follows.

As shown in FIG. 2, an electrophysiological signal is measured by the electrodes 5 and supplied to the sensing unit of the neurostimulator 3. In particular, the electrophysiological signal is measured across two electrodes 5b, 5c on either side of the electrode 5a to which the simulation signal is supplied. Accordingly, the electrophysiological signal is measured in bipolar mode. Taking a bipolar measurement between two electrodes 5b, 5c reduces movement artefacts and electromagnetic interferences (EMIs). This is often referred to as 'active shielding' (Reference 5) and achieves some reduction of stimulation artefacts, but a large proportion will still remain in the signal supplied to the neurostimulator 3 due to tissue and component asymmetries.

The neurostimulator 3 includes an electrophysiological processing circuit 20 arranged to process the electrophysiological signal and derive an LFP signal as a feedback signal in the following manner. The electrophysiological processing circuit 20 includes an analogue pre-processing section 21 and a digital post-processing section 22.

The pre-processing section 21 includes a pre-amplifier 24, an analogue antialiasing filter 25 and an analogue-to-digital converter (ADC) 26 arranged in series to pre-process the electrophysiological signal. The ADC 26 includes an internal digital antialiasing filter 27 and an analogue-to-digital conversion section 28. By way of example, in an externalised DBS system 1, the pre-processing section 21 may be a Porti 7 system from TMSi (Reference 5).

The pre-amplifier 24 is connected to the electrodes 5b, 5c and converts the bipolar electrophysiological signal into a single-ended form. The pre-amplifier 24 also pre-amplifies the electrophysiological signal by a relatively small gain (around 10-100) to avoid saturating the ADC 26. For instance, the pre-amplifier 24 may apply a pre-amplification gain of 20. The pre-amplifier 24 may be formed by plural stages, for example an initial differential amplifier and a subsequent pre-amplifier device.

To satisfy the Nyquist-Shannon sampling rule, antialiasing low-pass filtering compatible with the ADC sampling frequency used in the ADC 26 is implemented before further amplification and sampling (Reference 6). The analogue antialiasing filter 25 may be a simple first order low-pass filter with a −3 dB point at 4.8 kHz, which is supplemented by the digital antialiasing filter 27 of the ADC 26 which may be a sinc3 filter with a cut-off frequency of 0.27 times the sampling frequency. Where a Porti 7 system is used and configured at its maximum sampling frequency of 2048 Hz, the actual cut-off frequency of the digital antialiasing filter 27 is equal to 552.96 Hz.

Antialiasing filtering of the type performed by the analogue antialiasing filter 25 and the digital antialiasing filter 27 is conventional in DBS and is not sufficient to prevent the aliasing of the stimulation artefact caused by the stimulation signal, because the spectrum of the stimulation signal covers a wide frequency band.

The ADC 26, in particular the analogue-to-digital conversion section 28 of the ADC 26, samples the measured electrophysiological signal to generate a digital electrophysiological signal. The choice of the ADC 26 is important to derive an LFP signal of good quality. In particular, the ADC 26 has a high resolution to obtain a sufficient vertical resolution to adequately digitise the electrophysiological signals that can be around 1 μv or less despite the different sources of noises (thermal noise from the different electronic circuits, noises generated by the power supply and switching components, and noise from the room environment), and DC biases. For instance, the Porti 7 system uses a 22-bit ADC (Reference 7) and, for input signals on the range of ±150 mV, its vertical resolution is 1.4305 μV with an RMS noise<20 μV (Reference 5). However, the techniques described herein are not limited by the resolution of the ADC 26, offering high-precision neurophysiological recordings with a power consumption essentially dependant on the recording circuit technology, without saturation of the ADC 26.

The post-processing section 22 includes a notch filter 29, a large-band band-pass filter 30 and a narrow-band band-pass filter 31 arranged in series to process the digital electrophysiological signal output from the pre-processing section 21 and thereby extract the LFP signal of interest for the specific application.

The notch filter 29 removes the impact of mains interference (50/60 Hz) which usually remains in the electrophysiological signal despite the active shielding provided by the differential input.

The large-band band-pass filter 30 extracts the desired portion of the LFP spectrum and is used in applications requiring the analysis of a large portion thereof. This filter may be implemented by cascading: a high-pass filter (HPF) to remove the DC component of the signal, typically a 4th order HPF with a cut-off frequency at around 2 Hz; and a low-pass filter (LPF) with a cut-off frequency slightly above the maximum harmonic of interest, typically a 4th order LPF with a cut-off frequency at around 95 Hz. An alternative approach is to use a band-pass filter combining the characteristics of both filters.

The narrow-band band-pass filter 31 is particularly used in the case of closed-loop DBS since the goal is to reduce the amplitude of the beta-band peak that lies somewhere between 10–35 Hz but varying by patient and often being narrower than this range. The classical approach is to use a 4th order band-pass filter centred on the beta-band for closed-loop real-time applications, although offline post-processing is often based on wavelet analysis.

The notch filter 29, the large-band band-pass filter 30 and a narrow-band band-pass filter 31 are thus configured to remove noise, DC-drift and extract the frequency band of interest of the digitised LFP signal.

The post-processing section 22 therefore outputs the LPF signal as a feedback signal for use in the closed-loop control of the stimulation signal. To effect this control, the neurostimulator 3 includes a closed-loop deep brain stimulation control circuit 41 which is supplied with the LPF signal. The closed-loop deep brain stimulation control circuit 41 controls the operation of the stimulation generator 40 on the basis of the LPF signal. Any known closed-loop control algorithm may be used for example as disclosed in References 3 and 4. The closed-loop deep brain stimulation control circuit 41 supplies a primary control signal which controls the generation of the stimulation signal by the stimulation generator 40 and optionally also a waveform control signal which controls parameters of the waveform of the stimulation signal, for example the duration of each stimulation pulse, the gap between the stimulation pulses, the amplitude of the stimulation pulses, and/or the shape of the stimulation pulses.

In the simplest case, the primary control signal may simply turn the generation of the stimulation control signal on and off. Such control is implemented in the neurostimulator 3 shown in FIG. 2 by use of a selection unit 42. The primary control signal and the stimulation clock signal $f_p$ which controls the stimulation generator 40 to generate the stimulation pulses (as described further below) pass through the selection unit 42. Accordingly, the stimulation clock signal $f_p$ is passed when the primary control signal is high to cause operation of the stimulation generator 40 and is blocked when the primary control signal is low to cease operation of the stimulation generator 40. In the simplest case, the selection unit 42 may be an AND gate.

In more complicated cases, the waveform control signal may control the stimulation generator 40 in other ways, for example to also vary any of the parameters of the stimulation signal mentioned above.

The problem of the artefact induced on the electrophysiological signal by the stimulation signal in existing approaches will now be discussed in detail. This is one of the core problems in implementing a closed-loop stimulation despite the antialiasing filtering performed in pre-processing of the electrophysiological signal, for example as described above.

The presence of the artefact in the electrophysiological signal is an inevitable consequence of the stimulation signal delivered simultaneously to the site where electrophysiological signals are measured. The artefact leads to two main problems absent in the solution provided in the DBS device 1. A high voltage artefact is superposed on the useful LFP signal when the electrophysiological signal is sampled at a high frequency. Similarly, a low SNR, i.e. a high noise floor, is present due to aliasing when the electrophysiological signal is sampled at a low frequency.

Figure 4:
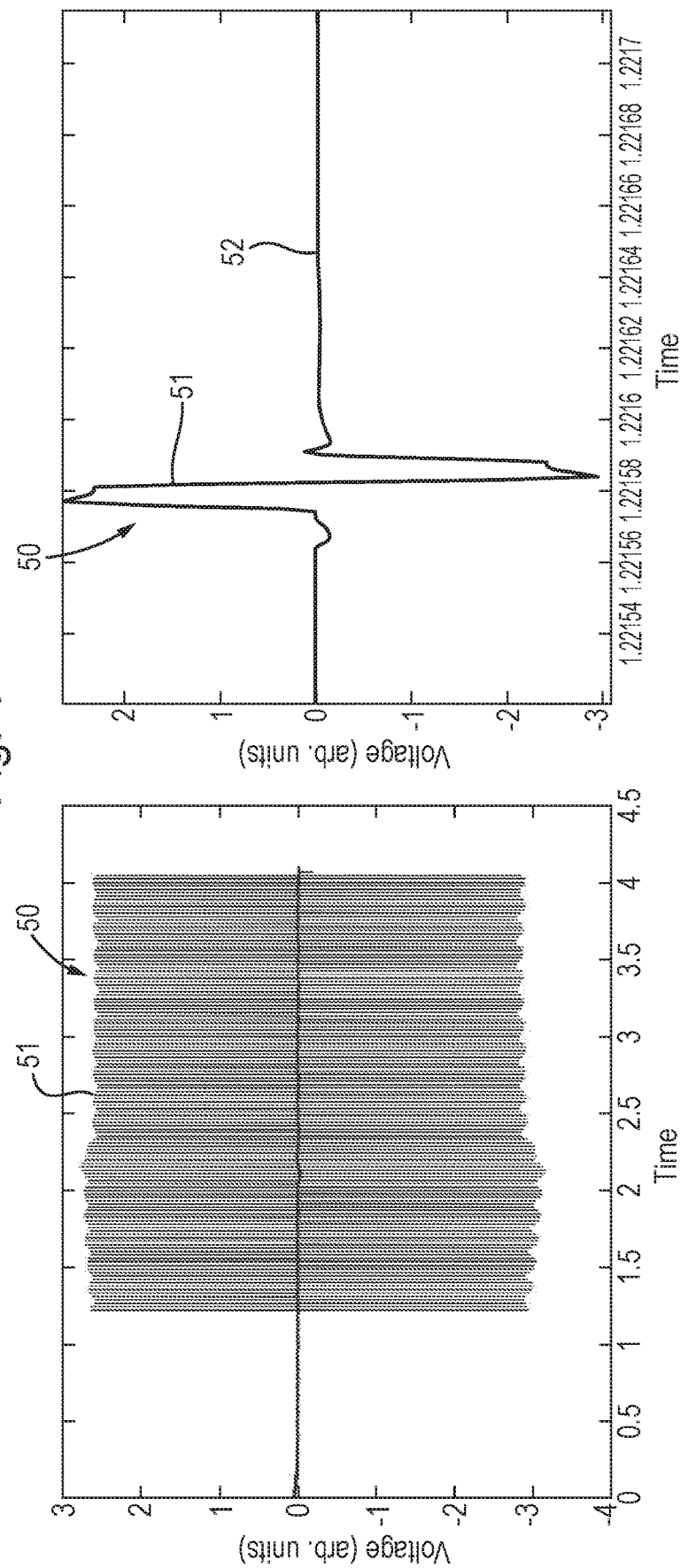
FIG. 4 is a pair of graphs of the electrophysiological signal sampled with a high sampling frequency over two different time scales, showing the artefact caused by the stimulation signal.

FIG. 4 shows a real-life example of the measured electrophysiological signal 50 sampled with a high sampling frequency of 44 kHz when the stimulation signal is switched on. Herein, the artefact 51 is clearly visible superimposed on the useful electrophysiological signal 52 which is typically around 1 μV. This artefact 51 has an amplitude around 1 volt and thus is around a million times greater than the amplitude of the useful electrophysiological signal 52 such that the level of the useful electrophysiological signal 52 cannot be seen on the scale of FIG. 4 needed to show the artefact 51.

As can be seen, the artefact 51 has the same overall shape as the pair of stimulation pulses of opposite polarity and is clearly derived therefrom but is shaped by the electrophysiological properties of the brain 8. The artefact 51 is in fact composed of harmonics multiple of the stimulation frequency as described in more detail below.

Figure 11:
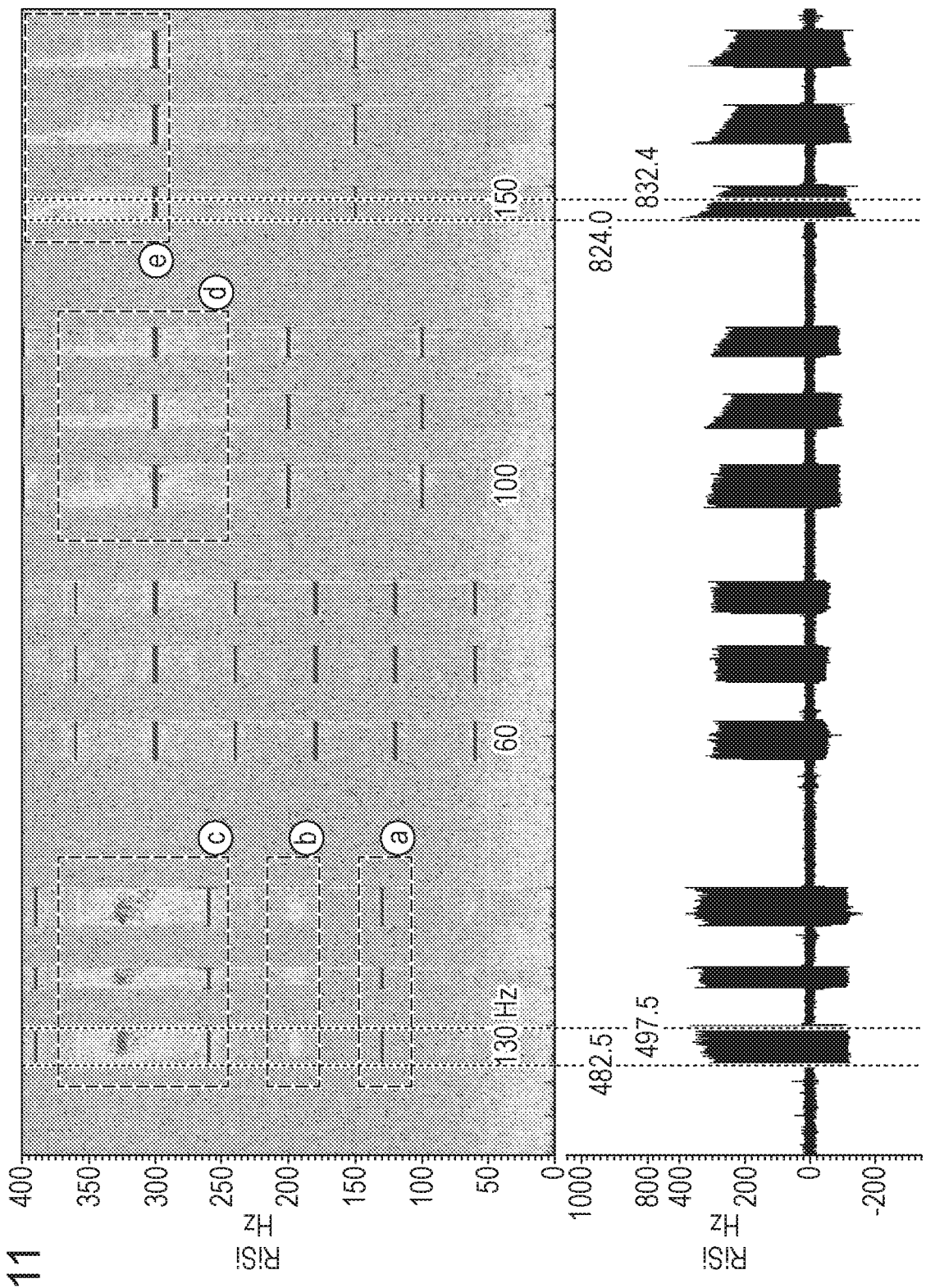
FIGS. 11 to 13 show recordings and artefact aliasing of an electrophysiological signals from three patients with PD using the same neurostimulator.
Figure 12:
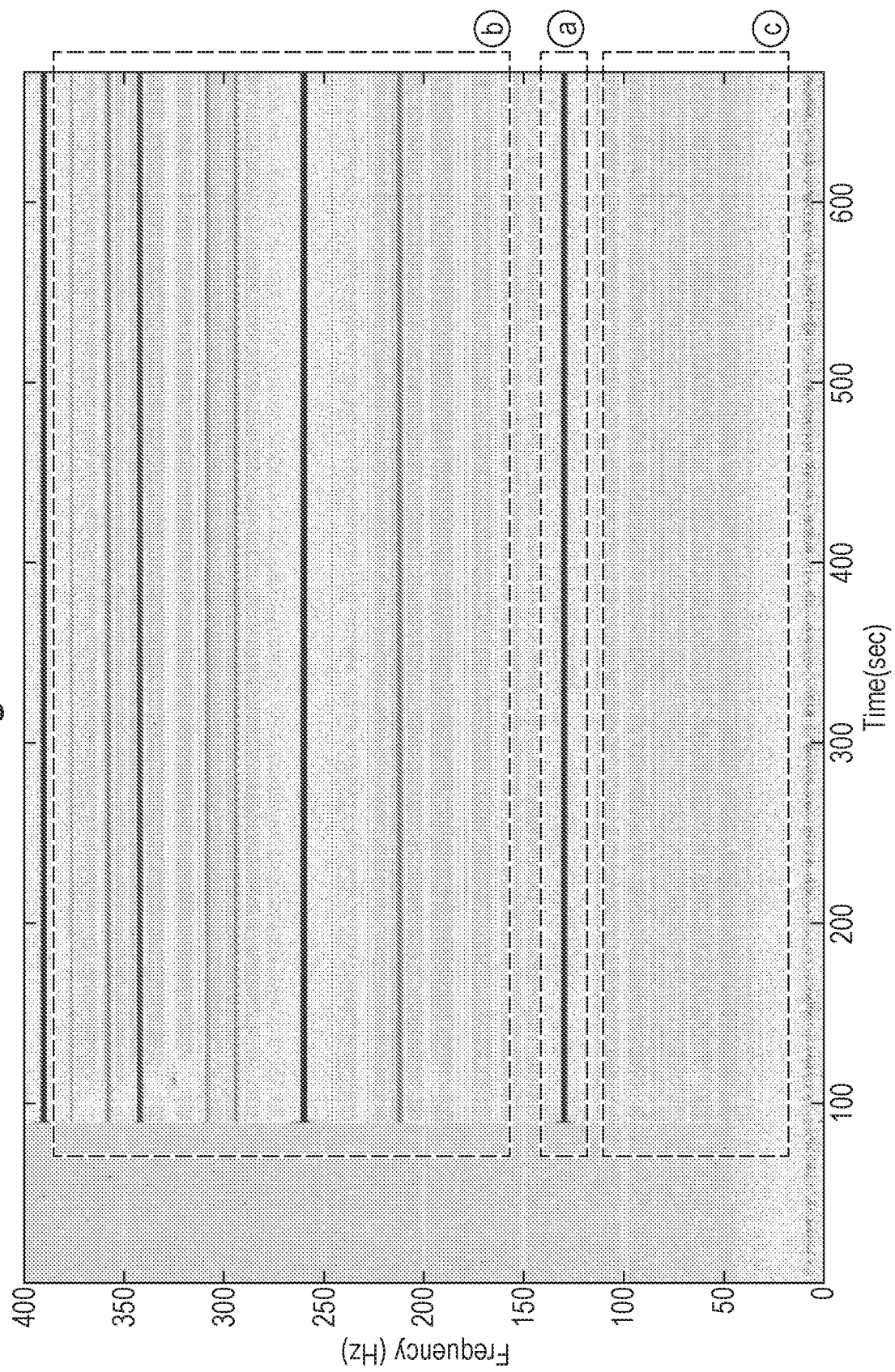
Figure 13:
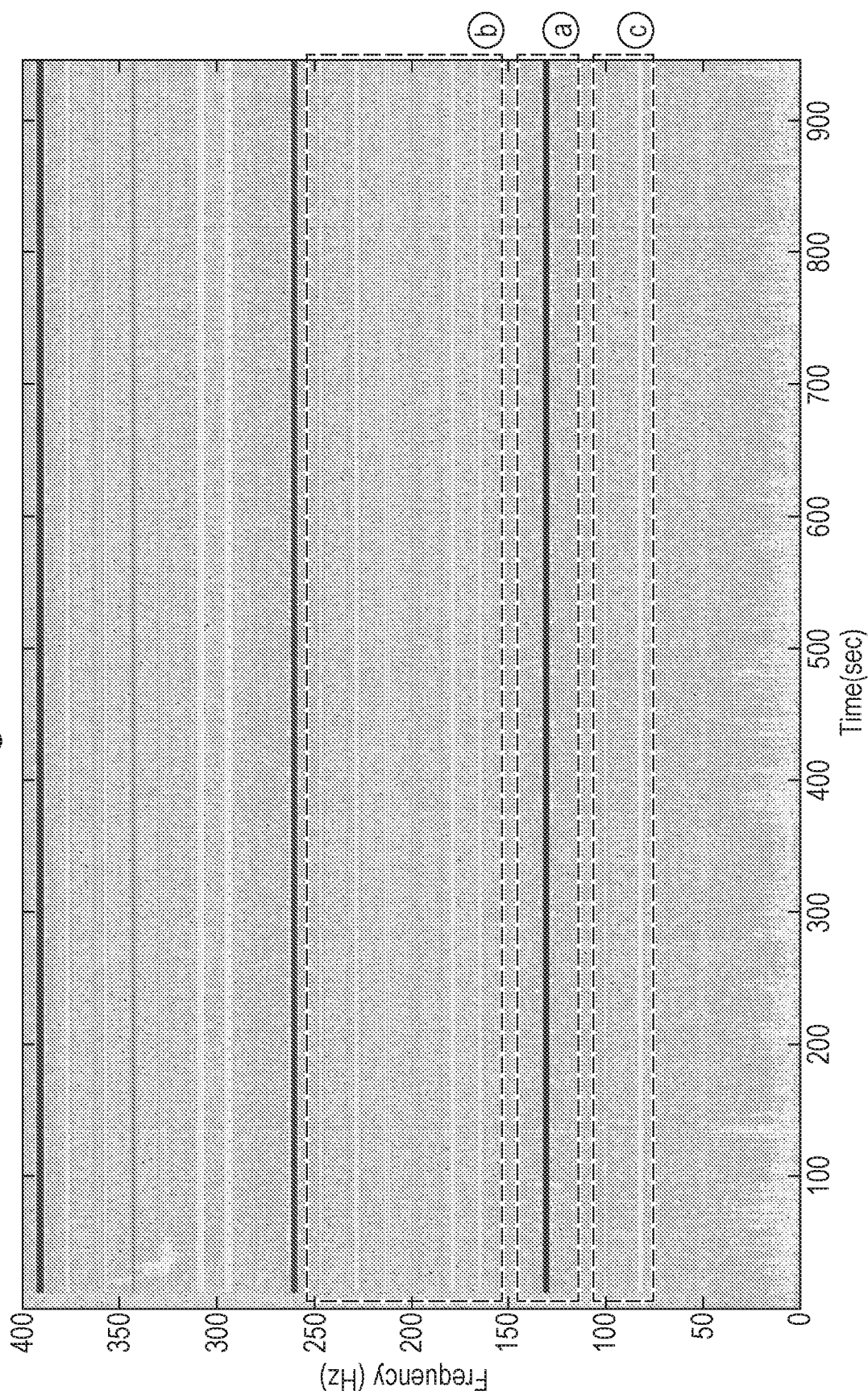

On the other hand, when a low sampling frequency is used, for example in the range from 500 Hz to 2 kHz as has often been used in DBS studies, then since the stimulation artefacts are composed of a very large range of harmonics multiple of the stimulation frequency stretching beyond the 600 kHz frequency band, the low sampling frequency could in principle lead to a widespread aliasing at frequencies different from the integer number of the stimulation frequency as shown in FIGS. 11 to 13 and described in more detail below, despite the implementation of an antialiasing filter around 500 Hz. This widespread aliasing can lead to an abnormally elevated noise floor and therefore a low SNR. This is illustrated in FIG. 5 wherein the first graph shows during simultaneous stimulation and recording, the frequency spectrum of the recorded electrophysiological signal in the absence of aliasing and the second graph shows the frequency spectrum of the electrophysiological signal in the presence of aliasing leading to an elevated noise floor.

Thus, the artefact makes it difficult to extract the LPF signal for closed-loop operation. Both the high superposed voltage artefact and the elevated noise floor represent important challenges to closed-loop stimulation because of the resultant amplitude of the measured electrophysiological signal is significantly distorted, highly variable, and difficulty to predict leading to misrepresentative thresholds and reference values used for implementing the algorithm of the closed-loop stimulation. In addition, the artefact 51 may saturate the pre-amplifier 24 and the ADC 26 used for digitising the measured electrophysiological signal.

The stimulation pulses of the stimulation signal delivered by the neurostimulator 3 is the principal source of the artefact observed during simultaneous stimulation and recording of the LPF signal. Although the shape of the artefact in the electrophysiological signal is slightly changed by the electrode and the brain tissue its main temporal and spectral characteristics remain comparable to the stimulation pulses generated by the neurostimulator 3. Therefore, temporal and spectral analyses of the raw stimulation signal applied to the brain 8 are important for closed-loop stimulation where the stimulation parameters are modulated dynamically, potentially simultaneously, by the control algorithm.

Spectral analysis of the stimulation signal was performed and the following results were obtained. For the analysis, a digital oscilloscope (PicoScope Model 5442A) with its corresponding software (PicoScope v6.13.3, published on May 10, 2018) was used to record all signals. This digital oscilloscope offers one 16-bit input or four 14-bit inputs at a sampling rate of 125 MS/s and a sample interval of 8 ns. The input range was set to ±10 V. The spectral analyses presented here used a 16-bit hardware resolution, 1.953 Mega Samples/second (MS/s) rate, and 512 ns sample interval. Also, there was used a "Flat-top" Fourier spectral decomposition method, 524288 number of bins, a time gate of 536.9 ms, which lead to 1.863 Hz bin width (or harmonic resolution). Since the flat-top windowing gives a better amplitude resolution with reduced spectral leakage than the Hanning window (which has a better frequency resolution) (Reference 8), it was chosen because the different harmonics of the stimulation pulses are known and exactly integer numbers of the stimulation frequency; thus, high frequency resolution is not required here.

There was used an analogue neuromodulator developed in-house, part of the intelligent deep brain stimulation (iDBS) comprising the proposed invention, to control four parameters of the stimulation signal which has the same general form as shown in FIG. 3, the controllable parameters being amplitude, frequency, pulse-width and pulse gap. An STN LFP emulator was used to collect the data presented herein.

Since the stimulation signal is a complex signal depending on four parameters, the stimulation pulses being 'convoluted' with another square signal, its spectrum is difficult to represent without a complex mathematical analysis. Hence the PicoScope capacity was used to calculate in real-time the Fourier spectrum of the stimulation signal, and to analyse how its power spectrum changes with four parameters. These analyses shed some light on the many phenomena encountered with stimulation artefacts.

The resulting frequency spectra are shown in FIGS. 6 to 10. Each of FIGS. 6 to 10 is a 3×3 grid of graphs of frequency spectra, wherein each column contains the same frequency spectra for a given set of values of the four parameters. To provide a comparison, in each of FIGS. 6 to 10 the central column in the same and corresponds to parameters of 3.5 V, 130 Hz, 60 µs pulse width and 20 µs gap, those being standard values of the parameters widely used in clinical application of DBS to treat PD. On the other hand, the left column shows the frequency spectrum when a parameter under consideration is decreased, and the right column shows the frequency spectrum when the same parameter is increased. The rows contain the frequency spectra with different frequency scalings and frequency ranges. In particular, the top row shows the range 0 to 600 kHz, the middle row shows the range 0 to 25 kHz, and the bottom row shows the range 0 to 10 kHz which focuses on the main spectral lobe.

Figure 6:
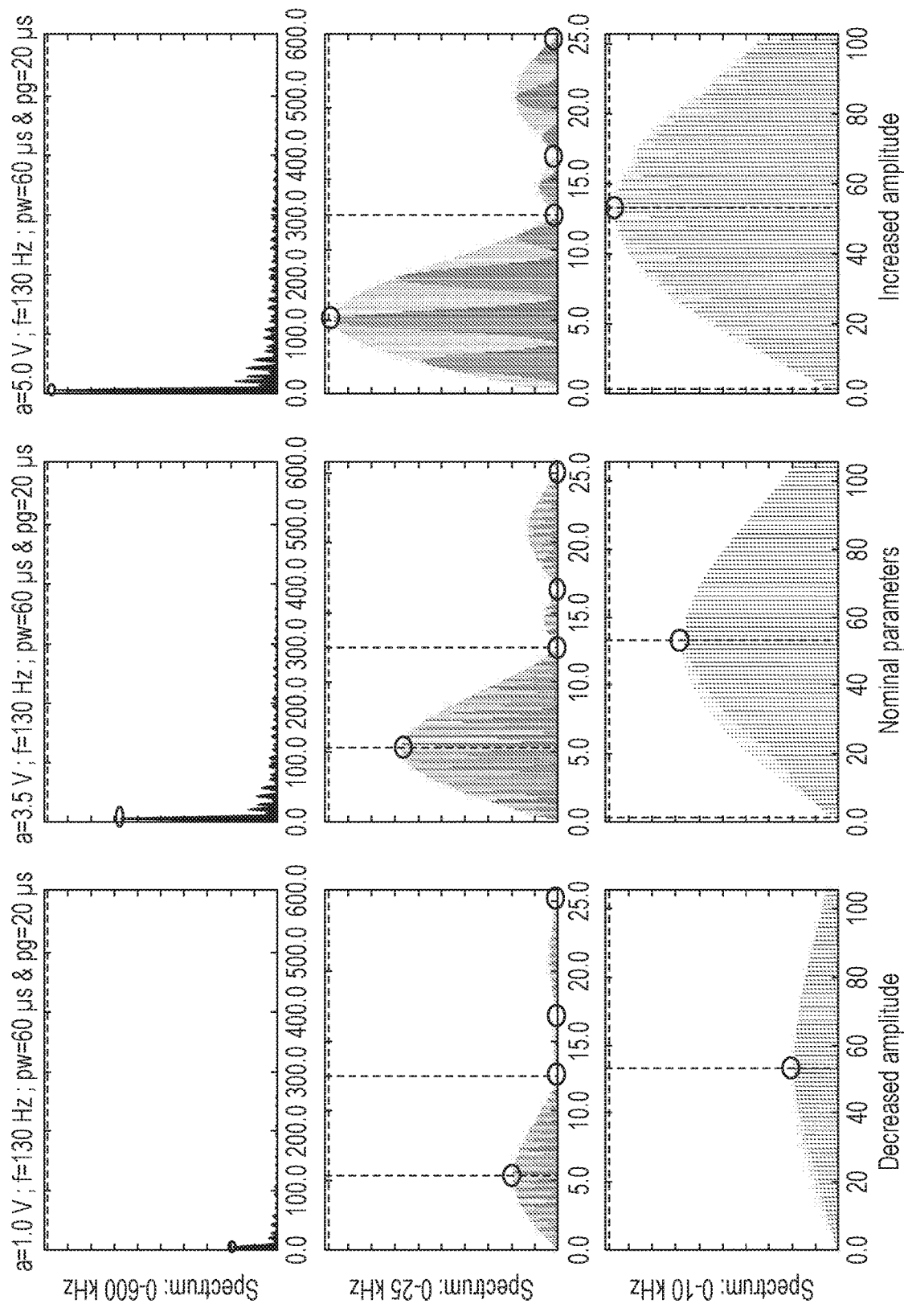
FIG. 6 is a grid of frequency spectra showing the spectral impacts of stimulation amplitude.

FIG. 6 shows the consequences of changing the amplitude to 1.0 V (left column) and to 5.0 V (right column). The most striking feature is that the spectrum has harmonics at all integer numbers of the 130 Hz stimulation clock frequency (cf. lower spectra row), multiplied by a complex sine cardinal (sync) function. When decreasing the amplitude to 1.0 V or increasing it to 5.0 V, the whole spectrum is reduced or amplified, respectively, by exactly the same factor. Meanwhile, changing the amplitude does not change the shape of the spectrum since the overall shape and nodes (harmonics with an amplitude close to 0) are kept identical.

Thus, the amplitude of the pulse has a linear relationship with the spectrum amplitude; this is not the case for other parameters as discussed further down.

Figure 7:
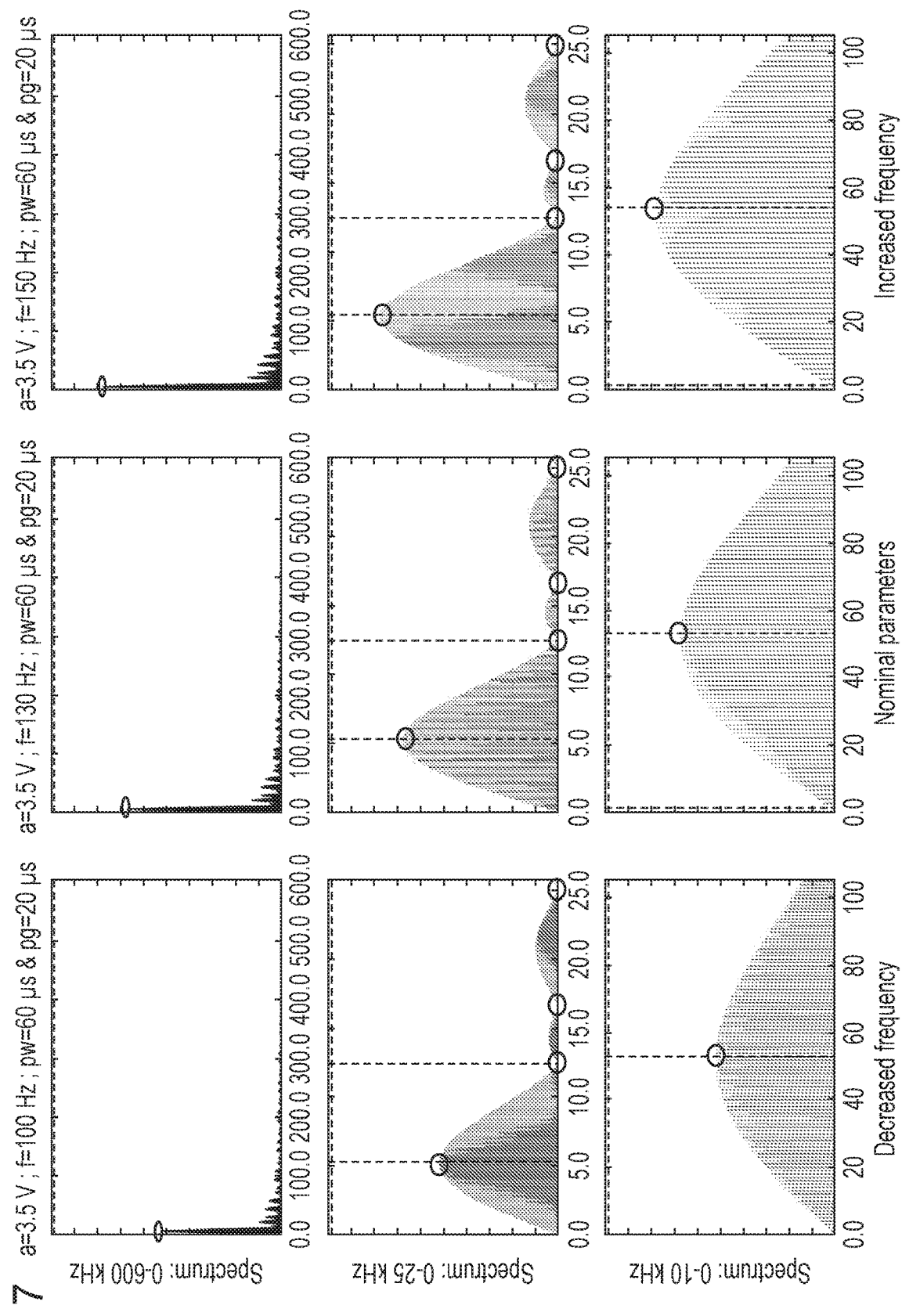
FIG. 7 is a grid of frequency spectra showing the spectral impacts of stimulation frequency.

FIG. 7 shows the consequences of changing the stimulation frequency to 100 Hz (left column) and to 150 Hz (right column). The obvious change is that the harmonics are now at each integer number of 150 Hz instead of 130 Hz as before. Also, changing the frequency does not change the overall shape of the spectrum, but only shifts its harmonics to the stimulation clock frequency, keeping the nodes at corresponding places, as seen in the middle and bottom rows of FIG. 7.

However, changes of stimulation frequency lead to changes in the amplitude of the harmonics as seen the middle and bottom rows. In particular, increasing the frequency (from 130 to 150 Hz) by a factor of 1.15 leads to an increase of ~1.11 in the amplitude of the peak harmonic as seen in the bottom row spectra, and decreasing by ~0.77 (from 130 to 100 Hz) leads to a decrease of ~0.85.

Thus, the stimulation frequency sets the harmonic frequencies, as well as impacts on the harmonic amplitude in a quasi-linear fashion. This implies that changing the stimulation clock frequency could lead to improvement or deterioration of aliasing.

Figure 8:
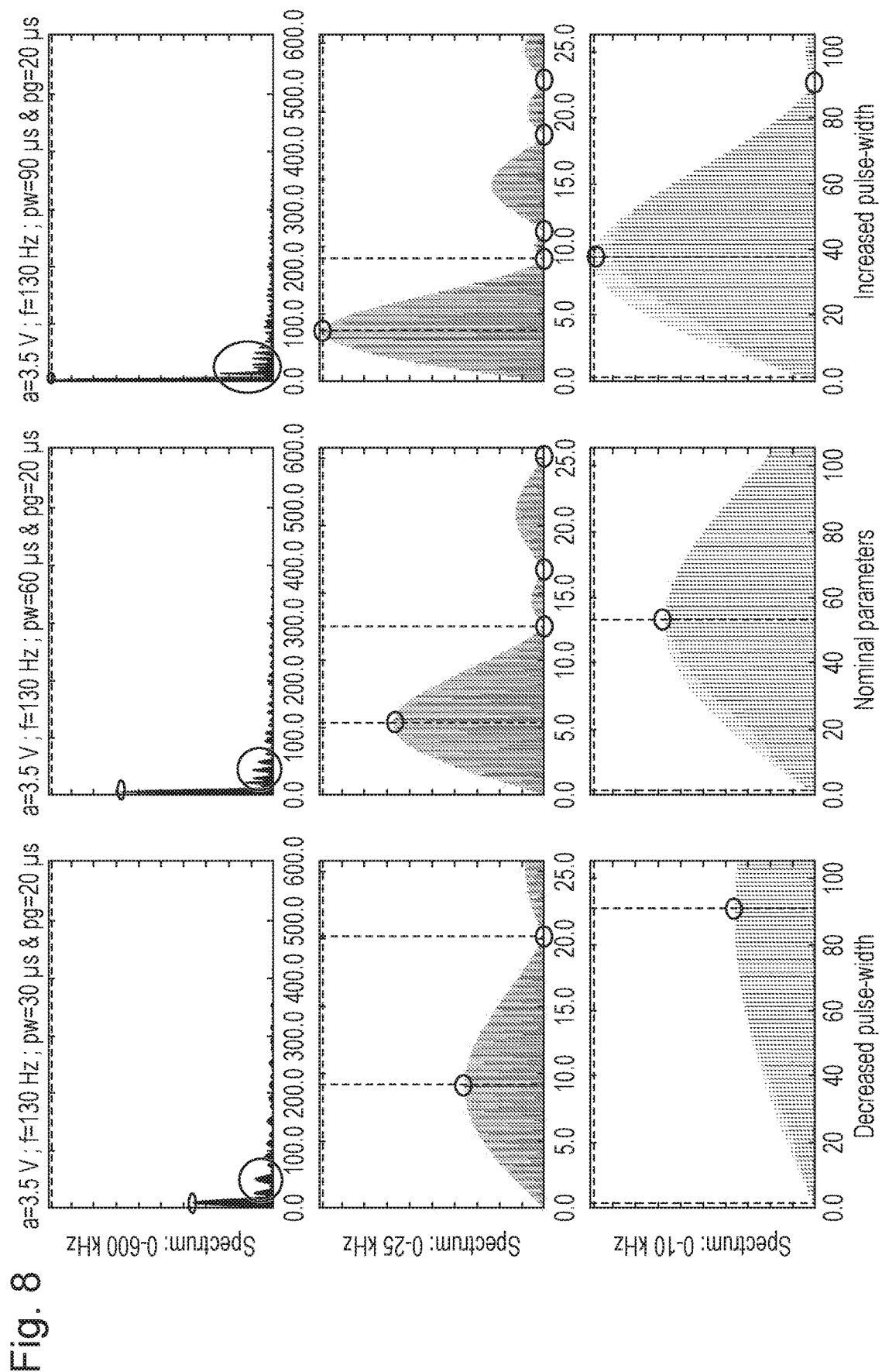
FIG. 8 is a grid of frequency spectra showing the spectral impacts of stimulation pulse-width.

FIG. 8 shows the consequences of changing the pulse-width to 30 µs (left column) and to 90 µs (right column). Those changes lead to a dramatic change in the overall spectrum envelope. Increasing the pulse-width leads to increase in the number of lobes over the same spectral range; therefore, compressing the lobes of the nominal case (c.f. top row of spectra of FIG. 8). While reducing the pulse-width reduces the number of lobes, therefore 'spreading' them without changing the spectral range.

Moreover, changes in the pulse-width also have a dramatic impact on the amplitude of the harmonics as seen in the middle row spectra of FIG. 8. In particular, an increase by a factor of 1.50 in the pulse-width (from 60 to 90 µs) leads to an increase of ~1.30 of the amplitude of the peak harmonic as seen in the bottom row spectra; and a decrease by 0.50 (from 60 to 30 µs) leads to a decrease of ~0.68.

Thus, the pulse-width sets the overall 'energy' and shape of the spectrum.

Figure 9:
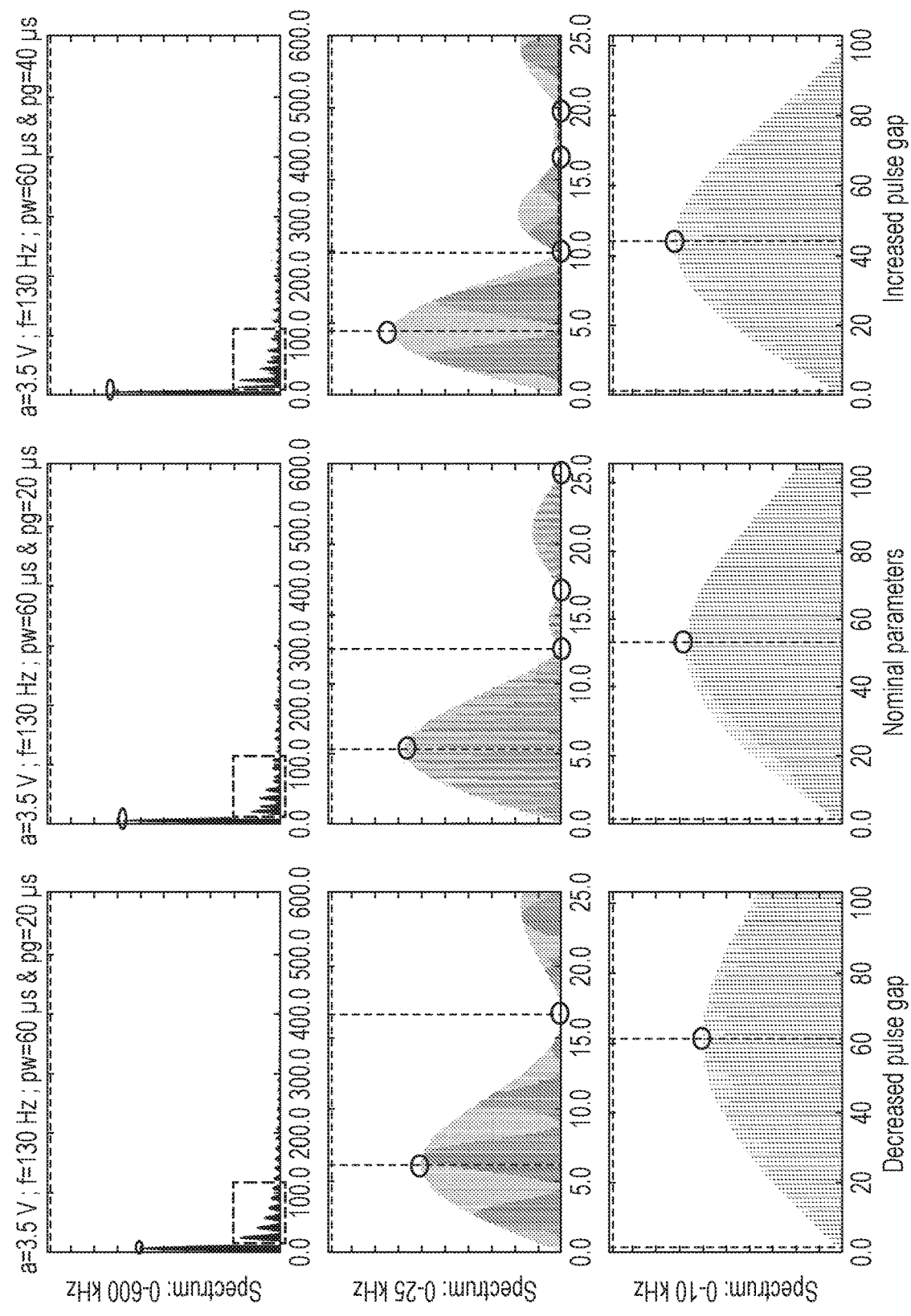
FIG. 9 is a grid of frequency spectra showing the spectral impacts of stimulation pulse gap.

FIG. 9 shows the consequences of changing the pulse gap to 0 µs (left column) and to 20 µs (right column). As for the pulse-width, changes of the pulse gap lead to a dramatic change of the overall spectrum envelope. Increasing the pulse gap increases the number of spectral lobes in the places not corresponding to the normal lobes of the sync function, whiles removing the pulse gap restore a 'smoother' sync spectral distribution in the same spectral range.

But contrary to the pulse-width case, changes in the pulse gap have a small impact on the amplitude of the harmonics as seen in the middle row spectra of FIG. 9. For instance, increasing by a factor of 2.0 the pulse gap (from 20 to 40 µs) leads to an increase of ~1.05 only of the amplitude of the peak harmonic as seen in the bottom row spectra.

Thus, the pulse gap is responsible for the rugged and non-regular aspect of the spectrum, and its differences from the regular distribution of the sync function.

Figure 10:
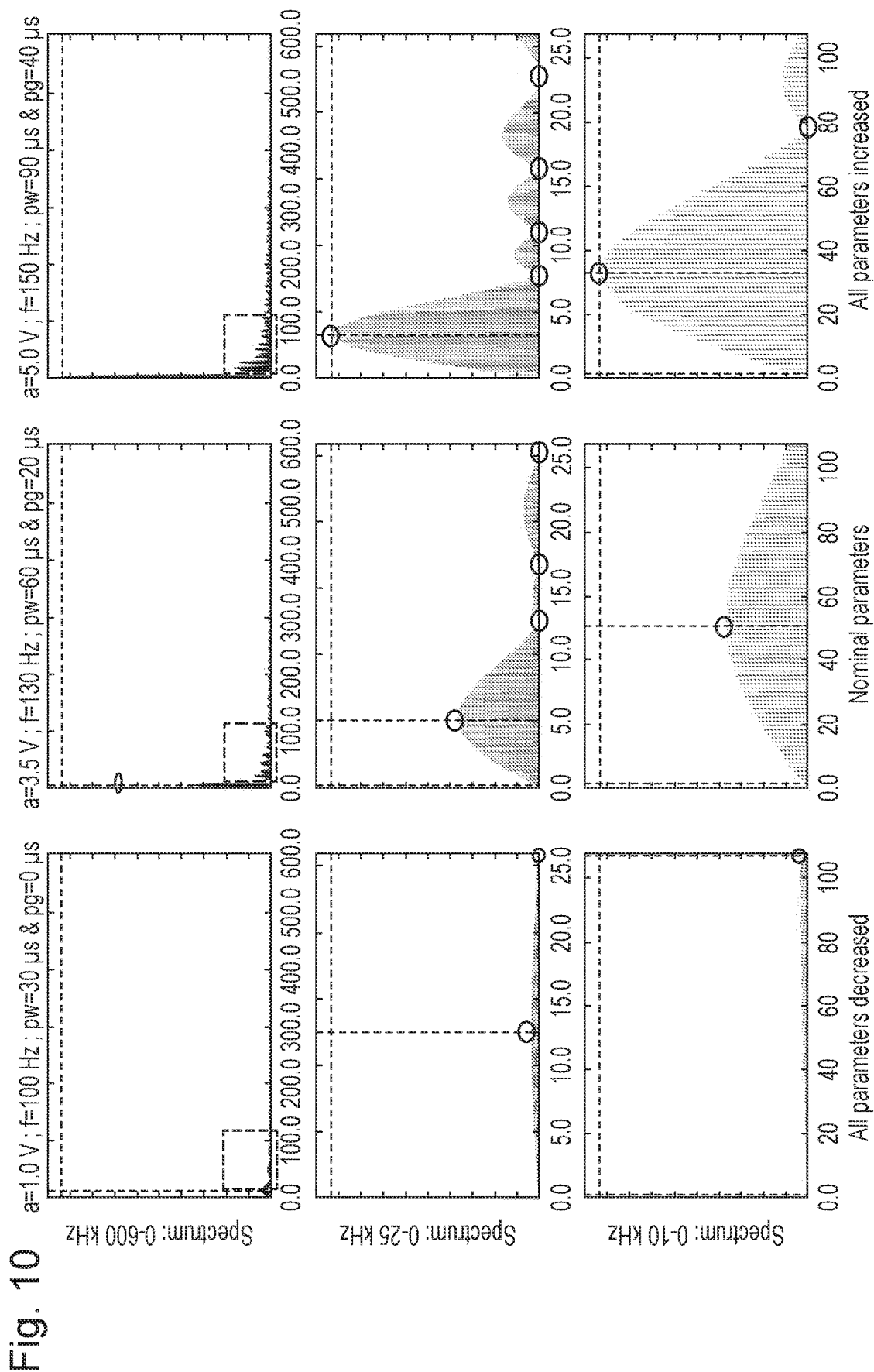
FIG. 10 is a grid of frequency spectra showing the spectral impacts of all four stimulation parameters.

To summarise, FIG. 10 gives a summary of the impacts on the spectrum of the four pulse parameters: amplitude, frequency, pulse-width and pulse gap. Simultaneous changes in these four parameters leads to dramatic changes in the spectrum as seen in the top spectra row. Changes in the pulse amplitude scale linearly with the amplitude of the spectrum. While the pulse frequency set the harmonic frequencies (all integer number of the pulse frequency are present), it also impacts the harmonic amplitude, but to a lesser degree than the pulse amplitude does. The pulse-width sets the overall spectral energy distribution as sinus cardinal (sync) function, whereas the pulse gap is responsible for the striking rugged and non-regular aspects of the spectrum.

It is hypothesised that the elevated noise floor often measured during simultaneous stimulation and recording, for example as shown in FIG. 5 results from the complex interaction between the pulse spectrum as defined by its four parameters, the antialiasing filters and the sampling frequency. This makes it very difficult to predict.

Such a complex interaction is illustrated by FIGS. 11 to 13 which show three actual recordings from three persons with Parkinson's disease (PD) using the same neurostimulator.

FIG. 11 shows the case of aliasing on recorded LFP signal of the same person over a six-minutes recording time when stimulated at 130, 60, 100 and 150 Hz successively. The top graph represents the temporal evolution of the spectrogram during simultaneous stimulation and recording, whiles the bottom the temporal data. The thick horizontal lines (box 'a') are the expected harmonics at integer numbers of the stimulation frequency. For example, stimulating at 130 Hz leads to expected red horizontal lines at 130, 290 and 390 Hz (and so son, and beyond 400 Hz). Some aliased harmonics appear also around 190 Hz (box 'b') and much more between the frequency range of 260-350 Hz (box 'c'). Stimulating at 60 Hz generated the expected integer harmonics (60, 120, 180 Hz and so on), but with limited aliasing elsewhere. Whereas, stimulating at 100 Hz generated aliasing in the 250-350 Hz band (box 'd'), and 300-400 Hz band with 150 Hz stimulation (box 'e').

FIG. 12 shows the case of aliasing on recorded LFP of a second person over a 16-minute period during simultaneous stimulation at 130 Hz and recording. The thick horizontal lines in the spectrogram are the expected integer harmonics of 130 Hz (box 'a'); the thin horizontal lines the aliased harmonics, which are above the 130 Hz stimulating frequency (box 'b'), but also below (box 'c').

FIG. 13 shows a dramatic case of widespread aliasing on recorded LFP of a third person over a 11-minute period during simultaneous stimulation at 130 Hz and recording. The thick horizontal lines again in the spectrogram are the expected integer harmonics of 130 Hz (box 'a'). This time, the thin horizontal lines are the wide-spread aliased harmonics, which are above the 130 Hz stimulating frequency (box 'b'), and go well below into the 15-30 Hz beta band of interest (box 'c').

It should be noted that the clearly visible aliased harmonics does not mean that there are no others aliasing harmonics, especially in comparison the 1 µV amplitude of the useful electrophysiological signal.

The neurostimulator 3 overcomes these problems using an approach in which the generation of stimulation pulses in the stimulation generator 40 and the sampling of the electrophysiological signal by the ADC 26 are synchronised, with control of the relative phase to cause the sampling to occur outside the stimulation pulses, or in other words the conversion time (or settle time) of the ADC 26 occurs outside the stimulation pulses. As will now be described with reference back to FIG. 2, this is achieved by a relatively simple configuration of the neurostimulator 3 to effect the synchronisation and relative delay of the sampling clock signal that is supplied to the ADC 26 and the stimulation clock signal supplied to the stimulation generator 40.

This works because the ADC 26 performs the sampling at timings controlled by the sampling clock signal and the stimulation generator 40 generates the stimulation pulses at timings controlled by the stimulation clock signal. Typically, the sampling clock signal and the stimulation clock signal are periodic square signals, and the sampling of the electrophysiological signal by the ADC 26 occurs over a conversion time (or settle time) starting at a timing of the rising edge of sampling clock signal whereas the stimulation generator 40 generates the stimulation pulses at the rising edge of the stimulation clock signal. Thus, control of the clock signals similarly controls the operation of the ADC 26 and the stimulation generator 40.

Specifically, the synchronisation and relative delay is achieved as follows. The neurostimulator 3 includes a master clock 60 that generates a master clock signal of frequency $f_m$ and a clock signal unit 61 that derives the sampling clock signal of frequency $f_s$ and a stimulation clock signal of frequency $f_p$ therefrom. The master clock signal is a periodic square signal.

The clock signal unit 61 supplies the master clock signal directly to the ADC 26 as the sampling clock signal, so the sampling clock signal is the master clock signal and the frequencies $f_s$ and $f_m$ have the same value.

The clock signal unit 61 includes a frequency divider 63 and a delay unit 64.

The master clock signal is supplied to the frequency divider 63. The frequency divider 63 frequency divides the master clock signal by a plural integer value N to derive an initial stimulation clock signal of frequency $f_r$ which has a value of $f_s/N$ which is supplied to the delay unit 64. The frequency divider 63 may be a modulo-N frequency divider.

The delay unit 64 delays the first stimulation clock signal to derive the stimulation clock signal of frequency $f_p$ which has the same value as frequency $f_r$. The value of the delay time $D_t$ as at least the time the ADC 26 requires to fully complete the analogue-to-digital conversion, for example being of the order 10 μs to 20 μs in a standard ADC, or being less than 1 μs in a faster ADC. It should be noted however that the delay is not of absolute necessity for the proper functioning of the proposed solution; it represents a safeguard to guaranty that the ADC circuit 26 never sees at its inputs the artefact whiles performing the actual digital conversion. Since most ADCs come with an internal sample-and-hold function that memorises/holds the analogue input to be converted to the value it was at the rising-edge, the memorised/held analogue value is not influenced by any further variation of the input signal to be converted.

Thus, the sampling clock signal and the stimulation clock signal are intrinsically synchronised because they are both derived from the master clock signal. Also, a relative delay between the sampling clock signal and the stimulation clock signal is introduced, in this example by the delay unit 64 delaying the initial stimulation clock signal, i.e. after performing the frequency dividing.

Figure 14:
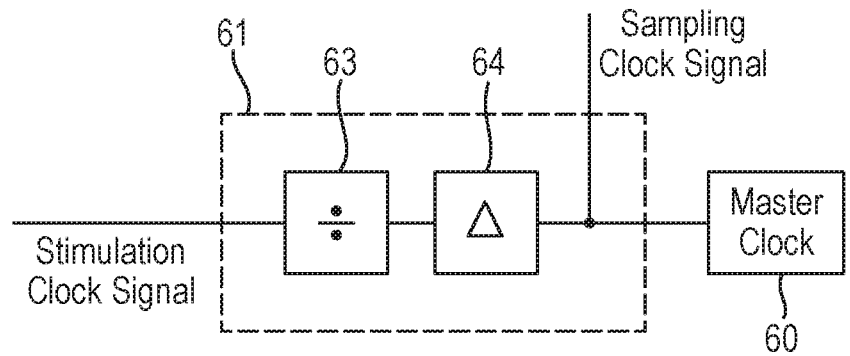
FIGS. 14 and 15 are diagrams of alternative configurations for the clock unit of the neurostimulator of FIG. 2.
Figure 15:
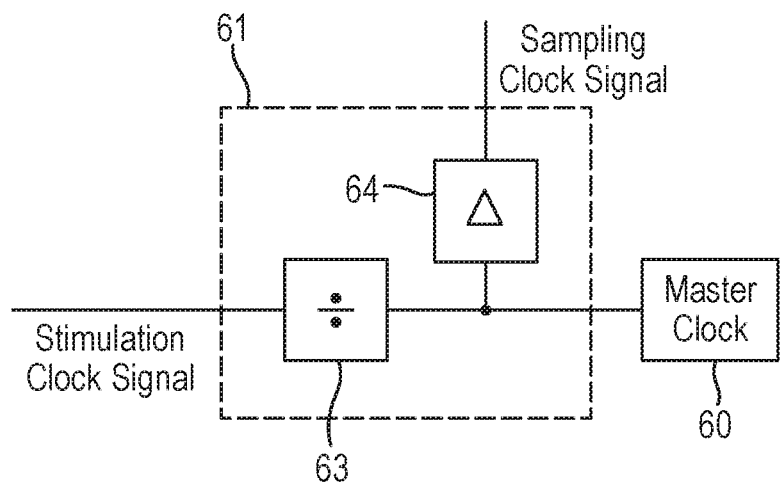

However, the relative delay between the sampling clock signal and the stimulation clock signal may be introduced by arranging the delay unit 26 at other locations. For example, FIGS. 14 and 15 show alternative forms of the clock signal unit 61. In each case, the sampling clock signal and the stimulation clock signal are derived from the master clock signal in a similar manner and so are synchronised. However, in FIG. 14 the delay unit 64 is arranged to delay the master clock signal before supply to the frequency divider 63 to derive the stimulation clock signal. In contrast, in FIG. 15 the relative delay is introduced by arranging the delay unit 64 to delay the clock signal obtain from the frequency divider 63 to derive the stimulation clock signal. In this case, it is important to note that, in order to cause the sampling to occur outside the stimulation pulses, the magnitude of the delay introduced by the delay unit 64 in FIG. 15 is different from the case of FIGS. 2 and 14 because the clock signal from the frequency divider 63 is delayed.

As can be seen, the clock signal unit 61 implements this control in a simple manner requiring minimal electronics. In particular, the clock signal unit 61 may be implemented at the software level of the neurostimulator 3.

Figure 16:
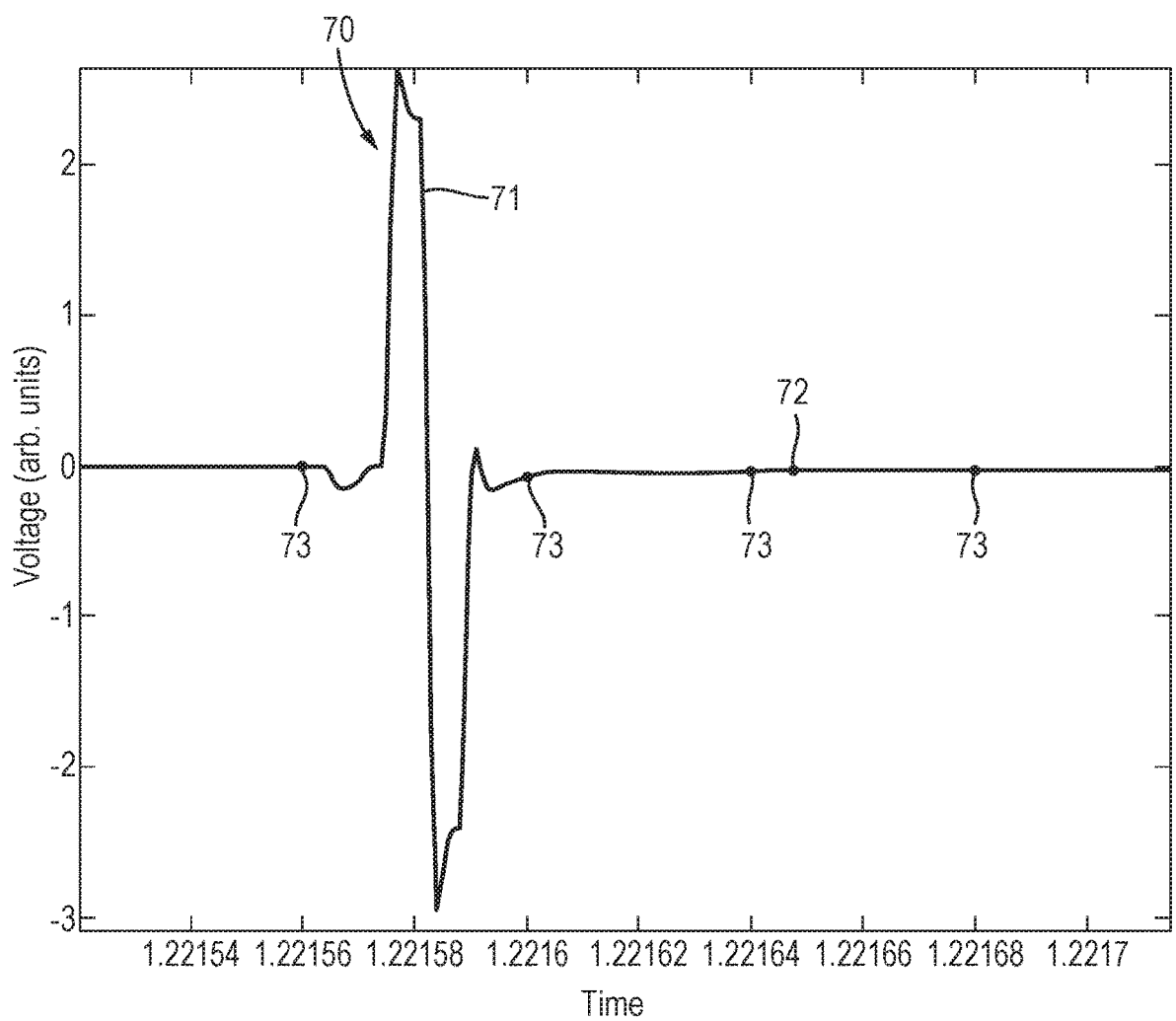
FIG. 16 is a graph of the electrophysiological signal showing the artefact caused by the stimulation signal and the timing of sampling.

The relative delay is selected having regard to the duration of the stimulation pulses of the stimulation signal and to the conversion time (or settle time) of the ADC 26 to cause the sampling to occur outside the stimulation pulses. This principle is illustrated in FIG. 16 is a graph of the electrophysiological signal 70 showing the artefact 71, at the timing of the stimulation pulse, the useful electrophysiological signal 72 and the timings 73 of the sampling. The artefact 71 generated will last for substantially the same period of time as the stimulation pulses of the stimulation signal. Strictly speaking, this does not include the transient DC-drift that is also generated at the end of the stimulation (cf. FIG. 11), which can be removed by the filtering in the post-processing section 22 after digitisation, and/or removed by specific discharging electronic circuitry (Reference 9).

In this example, the relative delay has been selected so that the timing 73 of one sample occurs just before a stimulation pulse is delivered, so that the artefact 71 has ended by the timing 73 of the next sample as per Nyquist-Shannon rule. In FIG. 16, the timing 73 is illustrated as a point for clarity. In fact, the sampling has a conversion time (or settle time) over which sampling occurs, and the delay is selected so that the entire conversion time is outside the stimulation pulse and resultant artefact 71.

Subsequent samples occur at timings 73 until another stimulation pulse is delivered. As a result, the digital electrophysiological signal is not affected by artefacts from the stimulation signal, because the electrophysiological signal is sampled at a time when the stimulation pulses do not occur. Due to the synchronisation of the sampling clock signal and the stimulation clock signal, the same timings 73 relative to the artefact 71 are achieved for each pair of stimulation pulses. Without such synchronisation, there inevitably be coincidence of some timings 73 with the artefact 71 in some stimulation periods due to non-integer ratio between the sampling frequency and the stimulation frequency. Similarly, the relative phase also needs to be carefully selected so that the timing 73 of the sampling does not coincide with the artefact in each stimulation period which would of course increase, rather than decrease, the effect of the artefact 71.

Thus, the basic principle of this approach is to exploit the knowledge of the duration of the artefact, as described above, and at the same time comply with Shannon-Whittaker-Kotelnikov sampling theorem (Reference 27), and with the sampling synchronicity and stability required by the z-Transform (discrete Laplace transform) used in discrete control of discrete-time systems like in this case. Comparing to the blanking approach discussed above, the approach applied in the neurostimulator 3 does not have a recording recovery time per se since this is defined by the sampling frequency, which allows compliance with the Shannon theorem condition, and maintains the integrity of the requirements of the discrete Laplace transform necessary for closed-loop stimulation to work as defined by discrete control theory. Our invention is a key part of the intelligent deep brain stimulation (iDBS) proposed.

The sampling frequency $f_s$ is an integer multiple of the stimulation frequency $f_p$ and so is set by the desired stimulation frequency and the plural integer value N of the frequency divider 63. The plural integer value N is set to be high enough to enable the sampling frequency to provide coverage of the full bandwidth of the electrophysiological signal without aliasin components, while maintaining the effect of avoiding artefacts from the stimulation signal. Typically, the plural integer value N is at least one. For example, if the stimulation frequency takes a typical value of 130 Hz, then a plural integer of four provides a sampling frequency of 520 Hz, providing sampling of a bandwidth up to 260 Hz which is suitable for deriving the LPF signal for closed-loop DBS for the treatment of Parkinson's disease.

The sampling frequency is selected to set the sampling period (the inverse of the sampling frequency) to be longer than the total period of the stimulation pulses, including the gap between the stimulation pulses plus the conversion time of the ADC 26. In an illustrative example where the total period of the stimulation pulses is 120 μs, there is no gap between the stimulation pulses and the conversion time of the ADC 26 is 20 μs (labelled here a fast ADC although there do exist much faster ADCs), then the sampling frequency has an upper limit of $1/140$ $\mu s^{-1}$ which is around 7140 Hz.

This is not a significant constraint as current implementations of stimulation typically use a sampling frequency in the range from 500 Hz to 2000 Hz. In the above illustrative example, the highest possible plural integer value N is 54, giving a sampling frequency $f_s$ of 54×130 Hz=7.02 kHz and a sampling period of Ts=1/fs=143 μs, although in practice a lower plural integer value N is likely to be selected to provide a margin. By way of comparison, with a slower ADC that has a conversion time (or settle time) typically of around 250 μs (frequently found in high resolution ADCs), the total required time for the above illustration will be 370 μs (250 μs of settle time plus 120 μs of pulse duration). In this case, at a stimulation frequency of 130 Hz, the highest possible plural integer N is 20, giving an actual sampling frequency $f_s$ of 2.6 kHz and a sampling period of Ts=1/fs=385 μs approximately.

Figure 17:
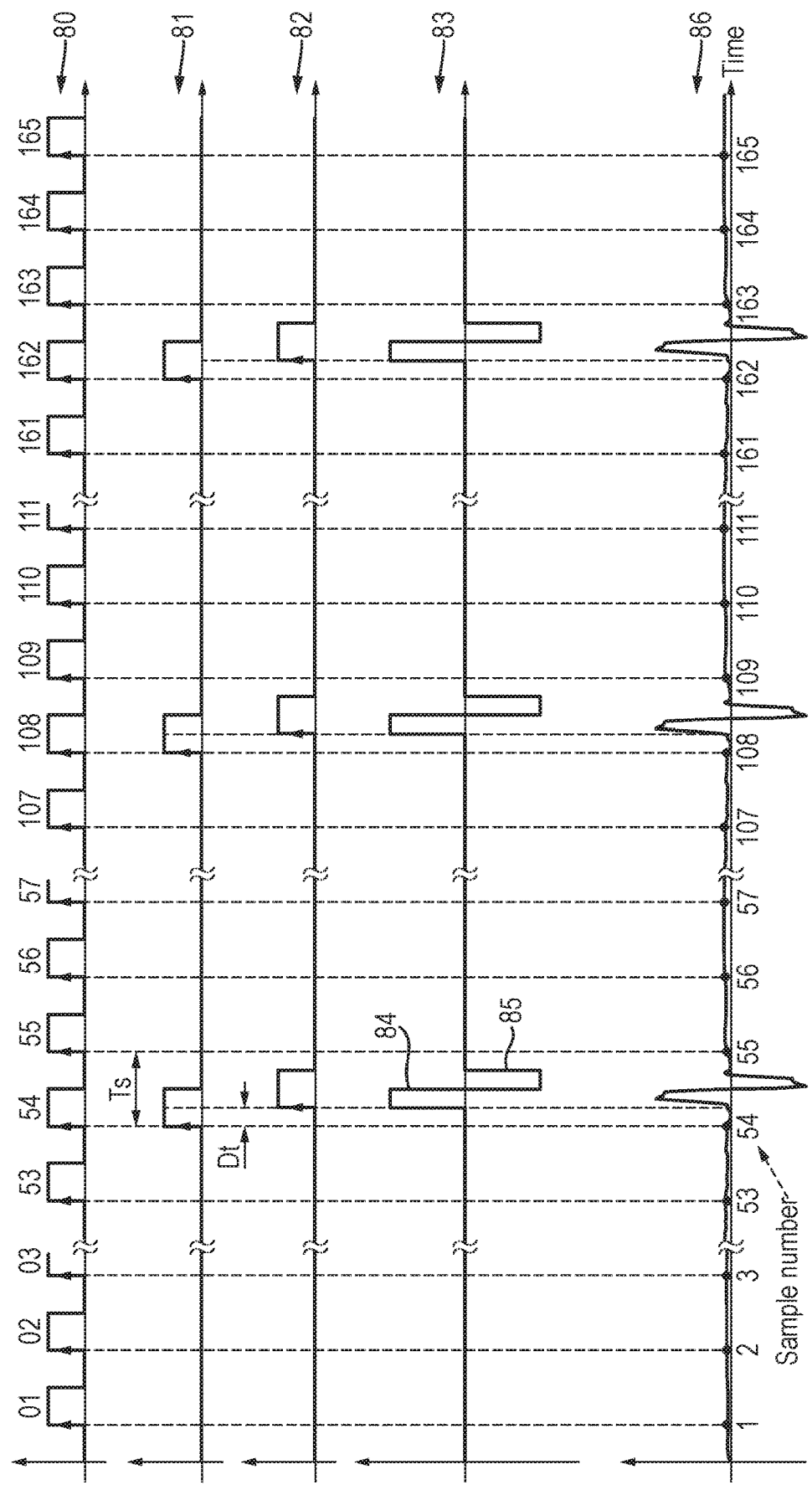
FIG. 17 is a chronogram of signals within the neurostimulator.

FIG. 17 shows a typical chronogram for these parameters of the first illustrative example (when using the example above labelled fast ADC) showing the master clock signal 80 which is also the sampling clock signal, the initial stimulation clock signal 81 output by the frequency divider 63, the stimulation clock signal 82 output by the delay unit 64, the stimulation signal 83 comprising a pair of stimulation pulses 84 and 85, and the resultant artefact 86. In this example, the time start is at t=0 for clarity. The master clock signal 80 is a square wave at the sampling frequency $f_s$ of 7.02 kHz. At each rising-edge thereof, the ADC 26 samples the measured electrophysiological signal, and at each modulo-N sample (54, 108, 162, etc.), a rising-edge is generated in the initial stimulation clock signal 81, which is then delayed by the specified delay $D_t$ to generate the stimulation clock signal 82. Then in turn, at each rising-edge of the stimulation clock signal 82, the pair of stimulation pulses 84 and 85 of total duration 120 μs is supplied to the STN, which induces the artefact 86 that takes the same form as shown in FIG. 4.

Since the sampling following after the pair of stimulation pulses 84 and 85 is is made some time after the artefact 86 has disappeared, the artefact 86 is not sampled.

Notes

This illustrative example, based on a sampling frequency $f_s$ of 7.02 kHz with the standard pulse duration, allows for high resolution data acquisition whilst removing the artefacts, and is therefore compatible with the oversampling technique classically used to improve SNR and ADC resolution. For example, for the same stimulation frequency $f_p$ of 130 Hz, the plural integer value N may be 10 giving a sampling frequency $f_s$=10×130 Hz=1.3 kHz, or the plural integer value N may be 20 giving a sampling frequency $f_s$=20×130 Hz=2.6 kHz, which is close to the sampling frequency of 2 kHz used with the TMSi device (References 5 and 7). Thus, when using the standard 60 μs pulse with 20 μs pulse gap at 130 Hz, and adding the ADC conversion time for guaranteeing a stable input signal (the latter condition of the ADC conversion time can ignored in some circumstances depending on the actual technology of the ADC adopted), the highest achievable plural integer value N is 48 and the sampling frequency $f_s$=48×130 Hz=6.24 kHz. Recent studies have shown that reducing the pulse duration to 30 μs instead of 60 μs used as standard results to a significantly larger therapeutic window, reduced side-effect whiles maintaining the same efficacy (Reference 13). Therefore, the sampling frequency upper limit is now $\frac{1}{60}$ μs$^{-1}$ which is around 16667 Hz; and adding again the ADC conversion time for security (as above this can be ignored with some ADC technologies), the highest achievable plural integer value N becomes 96 and the sampling frequency $f_s$=96×130 Hz=12.48 kHz; significantly increasing the range of sampling frequency available.

Another important feature of the neurostimulator 3 is that the synchronisation and relative delay can be fully implemented either by software code or with basic electronic components.

In the former, software alternative, the frequency divider 63 can be implemented by one of the internal timers of the microcontroller, and the delay unit 64 can be implemented by a simple for-loop that lasts for the required delay, or by a set of 'Nop' instructions. The possibility to be implemented at the software level means that currently reprogrammable implanted devices can be easily 'patched' to implement this invention, without the need to make any hardware change.

In the latter hardware case, the frequency divider 63, the delay unit 64 and the selection unit 42 may be arranged as follows using basic electronic components readily available, although this is for illustration and alternatively a custom-made implementation using FPGA techniques is possible and may improve physical footprint and technical performance.

Figure 18:
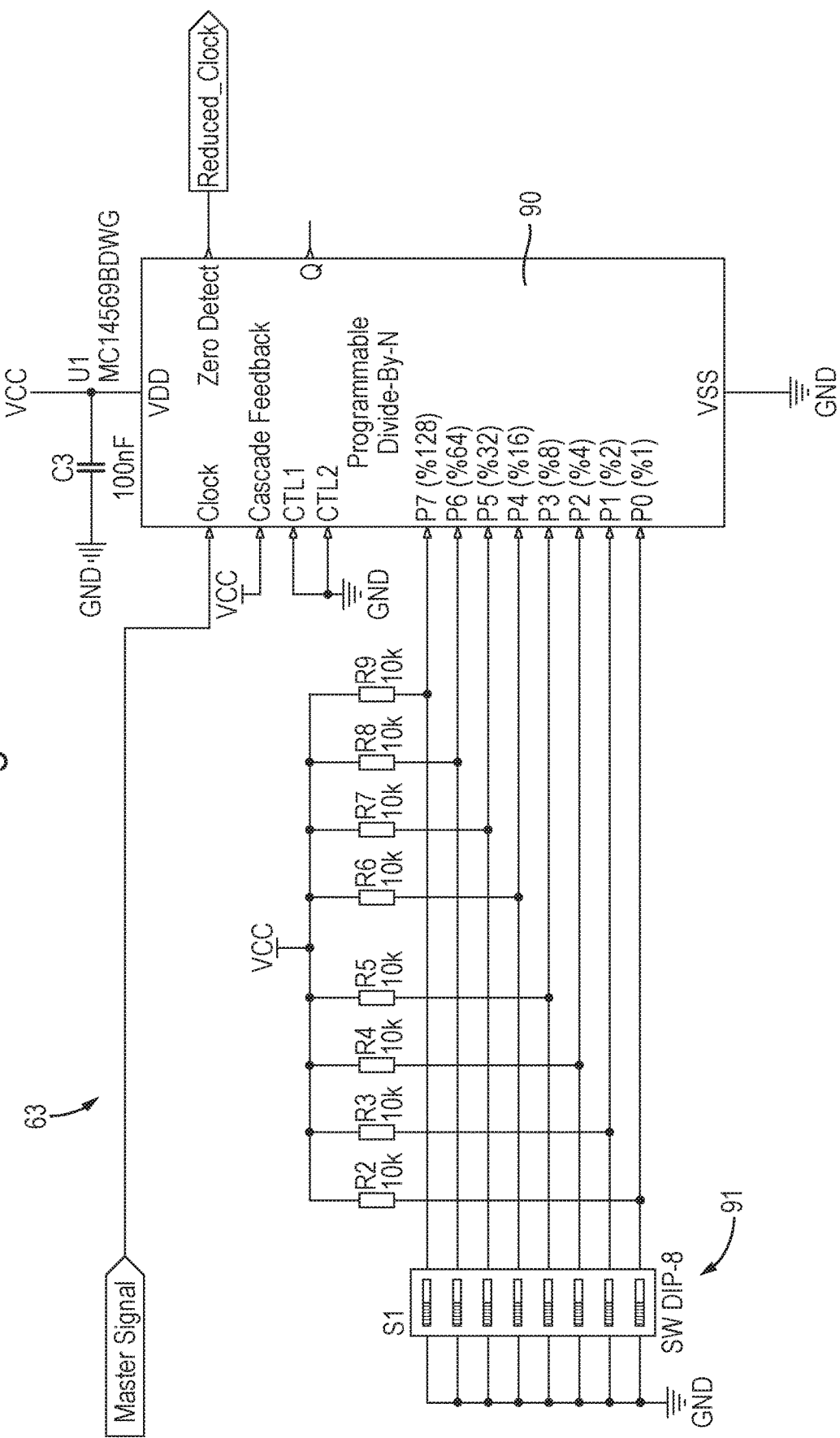
FIG. 18 is a diagram of an electronic implementation of a frequency divider of the neurostimulator.

FIG. 18 shows an example of the implementation of the frequency divider 63 arranged as follows. The frequency divider 63 includes a programmable divide-by-N counter 90 to which the master clock signal is fed. The frequency divider 63 includes a set of switches 91 which is used to define the division ratio by an 8-bit number. For instance, for the illustrative example described above, to set the division ratio to n=54 in order to obtain a stimulation clock signal of frequency $f_p$=130 Hz with sampling clock signal of frequency $f_s$=54×130=7.02 kHz, the binary-coded decimal word used on the set of switches 91 is 01101100 (from LSB to MSB).

In practical implementation, typically only a few numbers of ratios between the master clock signal and the sampling clock signal would be necessary, in which case the circuit could be simplified.

Figure 19:
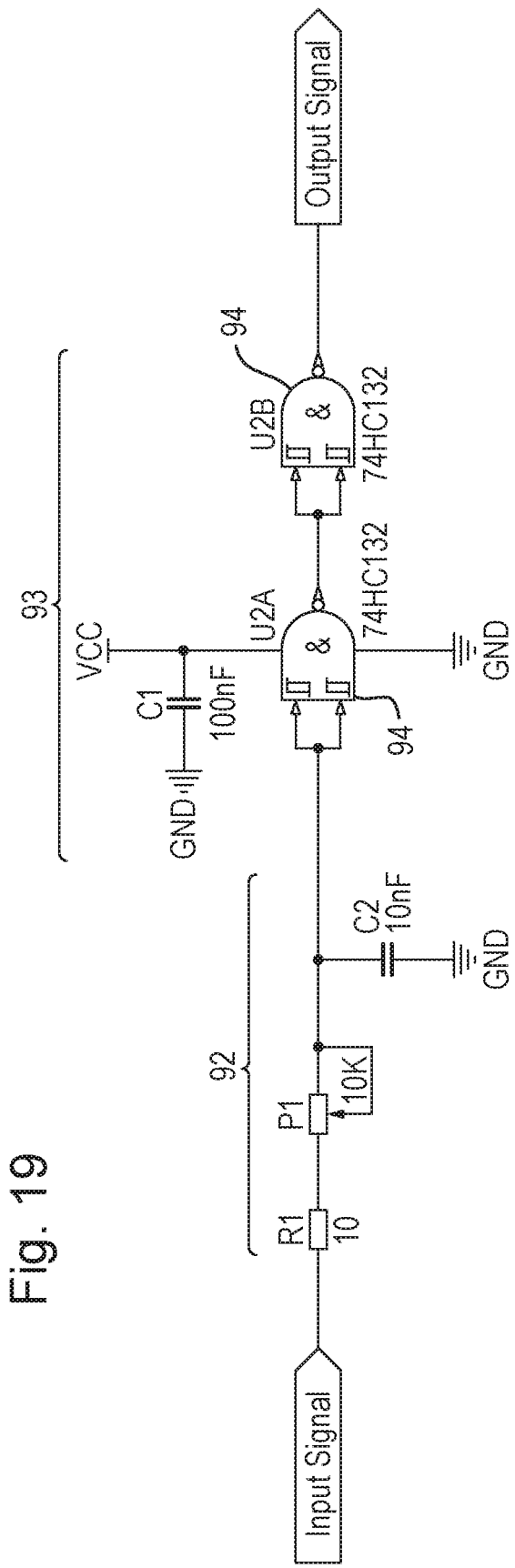
FIG. 19 is a diagram of an electronic implementation of a delay unit of the neurostimulator.

FIG. 19 shows an example of the implementation of the delay unit 64, based on a first order low-pass system. The delay unit 64 includes a delay setting section 92 and a level setting section 93. The delay setting section 92 uses a potentiometer P1 to set the delay, for example Δt=20 μs as per the illustrative example described above, which is fed to the level setting section 93. The level setting section 93 includes two Schmitt-trigger NAND gates 94 arranged in series to provide the generated signal with a logical level compatible with other digital circuits.

Figure 20:
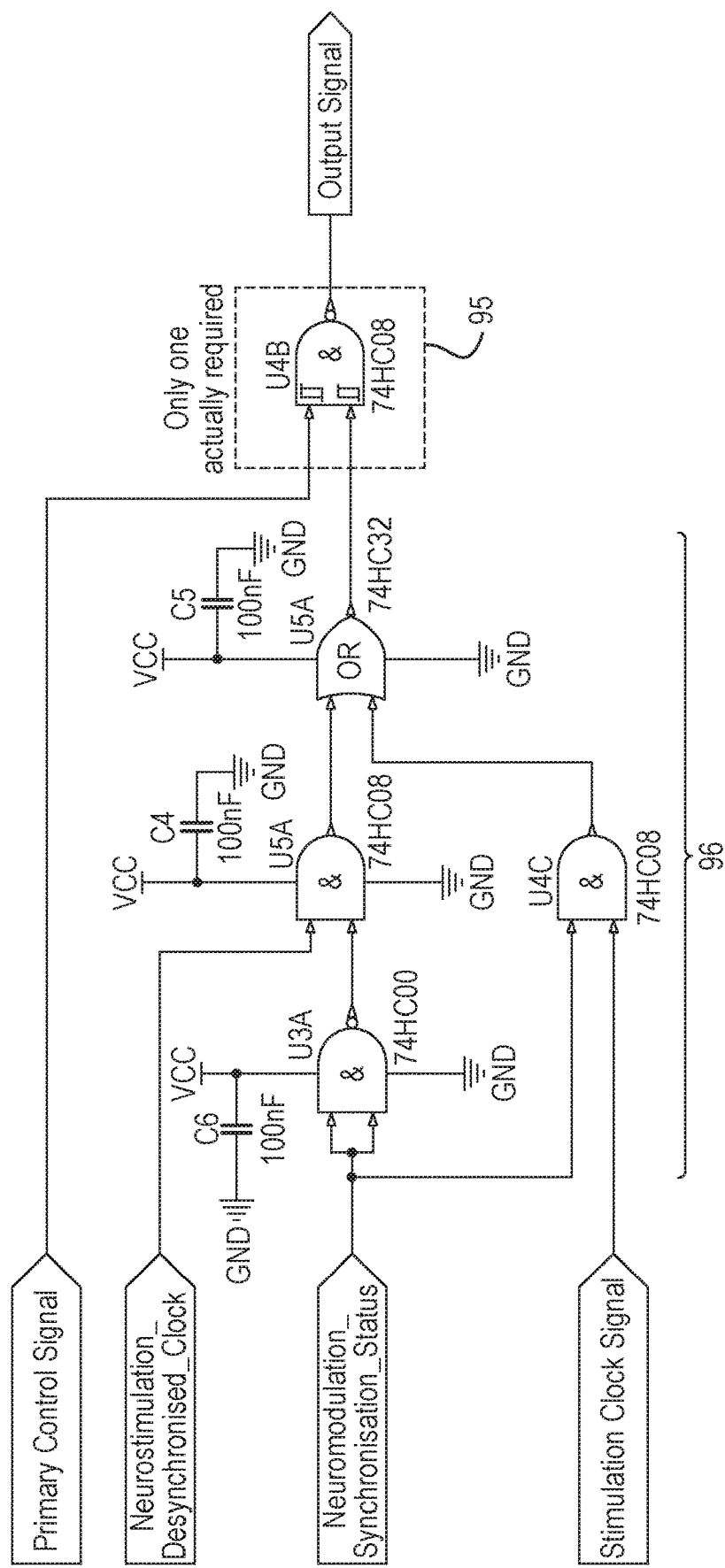
FIG. 20 is a diagram of an electronic implementation of a selection unit of the neurostimulator.

For better performance in terms of stability and temperature drift, other implementation is also possible using readily available designs (using for instance a voltage-controlled delay function, dedicated timing circuit or other equivalent approaches). FIG. 20 shows an example of the implementation of the selection unit 42. The main function of providing control on the basis of the primary control signal is provided by an AND gate 95 fed with the primary control signal and the stimulation control signal to block the stimulation clock signal when primary control signal is low. In this example, the selection unit 42 also includes a logical gate arrangement 96 which provides control in accordance with a neuromodulation synchronisation status and a neuromodulation desynchronised clock signal in order to be able to easily compare the analogue to digital conversion when synchronisation is enabled or disabled. However, in practical applications, this function may be reduced to a simple AND gate allowing to pass or block the synchronised stimulation clock signal when the primary control signal is set to 1 or 0, respectively.

Testing of the techniques disclosed was performed using the following implementation of the DBS device 1.

The frequency divider 63, delay unit 64 and selection unit 42 were implemented as shown in FIGS. 18 to 20.

The master clock 60 was implemented by a function generator (an AFG-2105). The ADC 26 was implemented by an Arduino DUE development board using the Arduino software (v1.8.9). This received an analogue input signal composed of the sum of a sinewave (representing the LFP recorded from the brain) and the stimulation pulse (generated by the neuromodulator). This analogue input was scaled into 0~3.0 V and has a DC offset of 2 V in order to comply with the Arduino Due analogue requirements. The ADC of the Arduino DUE development board received the sampling clock signal, and initiated an analogue to digital conversion at each rising edge, and then output the converted input signal to its DAC that was scaled between 0.5~2.0 V. The output DC offset was removed by an analogue subtractor and then the signal was amplified by an adjustable analogue gain in order to recover the original (digitised) input signal.

The post-processing section 22 was implemented by an analogue second-order Butterworth low-pass filter using a classical Sallen-Key circuit for illustration, with the cutting frequency set at around 300 Hz.

The stimulation generator 40 was implemented via a proprietary device capable of delivering a stimulation pulse at each rising edge of the stimulation clock signal. This device allowed the four parameters of the generated pulse, namely amplitude, frequency, pulse-width and pulse-gap to be set independently.

The testing was performed as follows. A sinewave of ±1 V at 20 Hz was used to represent the LFP signal recorded from the brain (representing here the beta-band signal of the LFP). The voltage pulse stimulation generated by the stimulation generator 40 was passed through an electrode-brain interface (EBI) circuit, modelling the temporal changes of the pulse due to the brain tissue to obtain artefact recorded close to that of presented by the literature. The resultant pulse was then added analogically to the sinewave after both signals were rescaled to reflect the difference in amplitude between the actual useful LFP signal and the artefact due to stimulation. In practice, the stimulation artefact is several thousand times larger than the useful signal, but for this testing it was restrained to being roughly 5 times bigger only.

The master clock signal was of frequency $f_m$=20.02 kHz, which was then divided by n=154 in order to obtain the synchronised stimulation clock signal of frequency $f_p$=130.0 Hz. The master clock signal was divided by 10 internally via the Arduino timer to provide the sampling clock signal of frequency $f_s$=2.02 kHz.

Results were recorded with a PicoScope 5442B from PicoTech, having a resolution of 14 to 16 bits hardware (and 18 to 20 bits software), a bandwidth of 60 MHz with its original tuned probe MI007, and using the PicoScope software v6.13.17.4271 (2019). The results were as follows.

Figure 21:
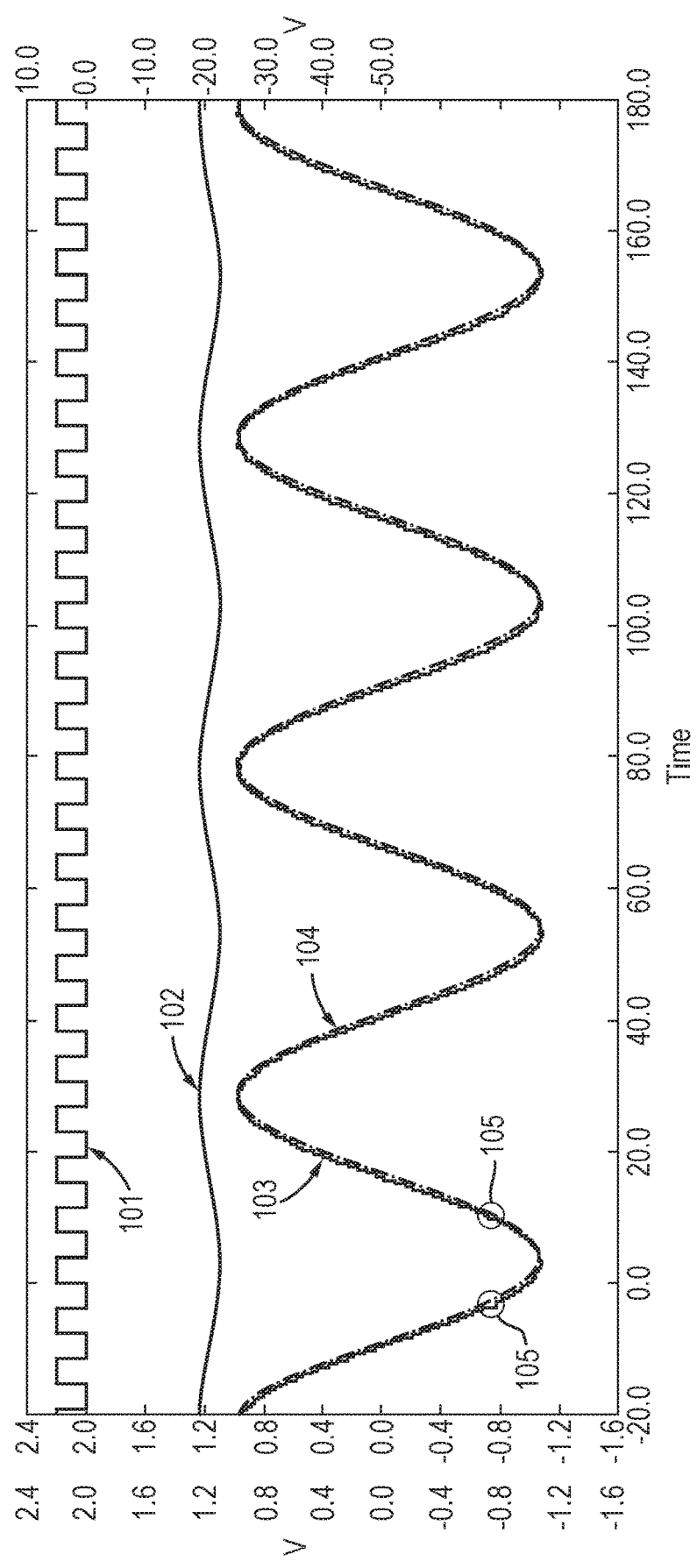
FIGS. 21 to 32 are graphs of signals obtained from a neurostimulator during tests using the implementations shown in FIGS. 18 to 20.
Figure 22:
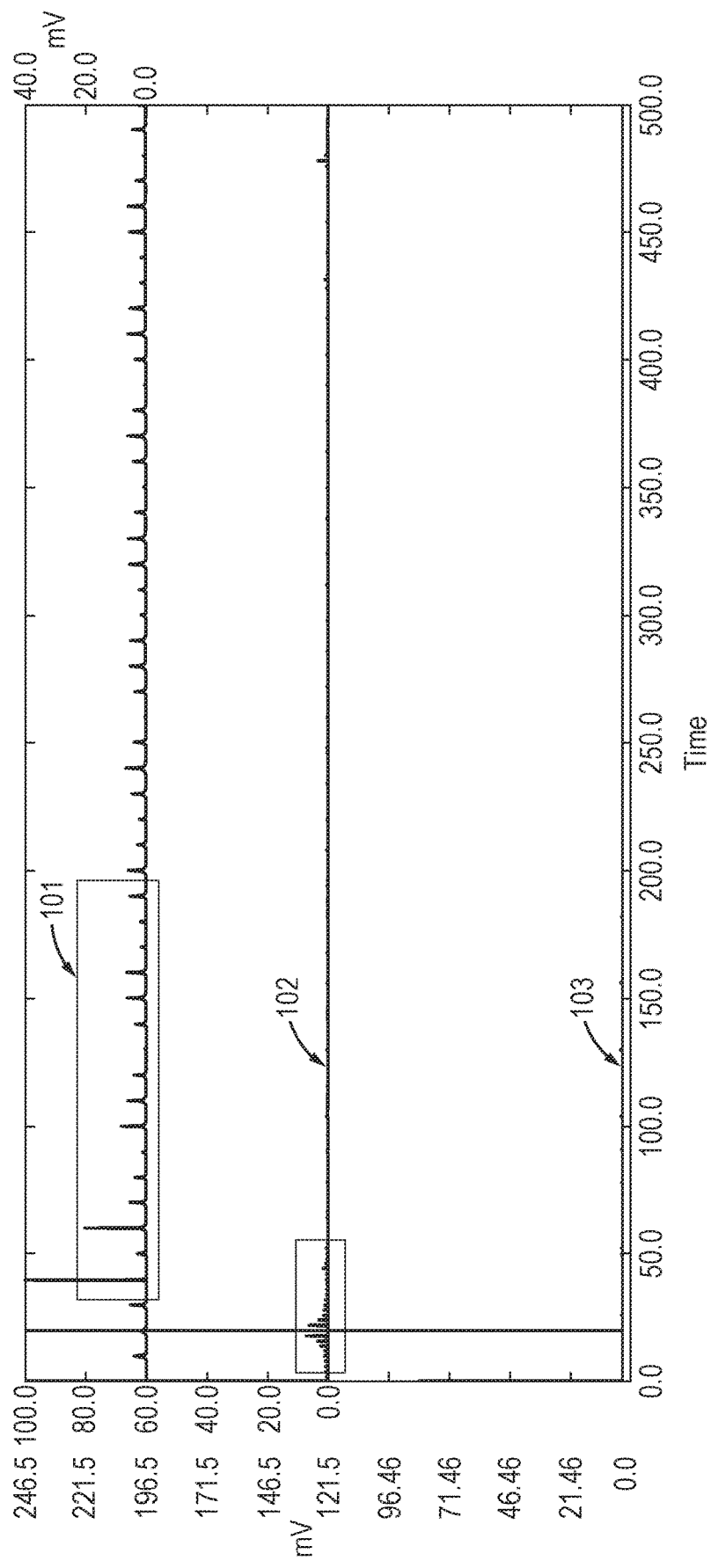

FIGS. 21 and 22 show results of a nominal case in the temporal domain and the frequency domain, respectively. FIGS. 21 and 22 illustrate the desynchronised stimulation clock 101, the analogue input 102 to the ADC 26, the discretised input 103 to the ADC 26, and the filtered discretised input 104 to the ADC 26. The nominal case represented the situation where the neuromodulation is turned OFF, i.e. an absence of the stimulation pulse in the input signal converted by the ADC 26 so that there is no recording artefact. This situation established the comparative condition, allowing characterisation of the background noise present, which is independent of the stimulation artefact.

Since the neuromodulation was disabled, no stimulation pulse was generated, and the analogue input 102 seen by the ADC 26 does not contain artefact. The discretised input 103 by the ADC 26 presented the expected stair-like effect due to digital conversion. However, one can see that some larger discretised values ("glitches") that do not correspond to the actual analogue input (see the black circles 105 in FIG. 21). Those "glitches" are due the harmonics present in the 'sinewave' input (generated digitally), and also to the background noise that was measured to be up to ±60 mV.

This was further confirmed by the spectrum on the nominal case as presented in FIG. 22, where the analogue input 101 has many high frequency harmonics, which then aliased around the 20 Hz harmonics of the sampled signal 102 (black dashed box in the green trace from FIG. 22). Those aliased harmonics are then significantly attenuated by the Butterworth filter of the filtered signal 103.

Figure 23:
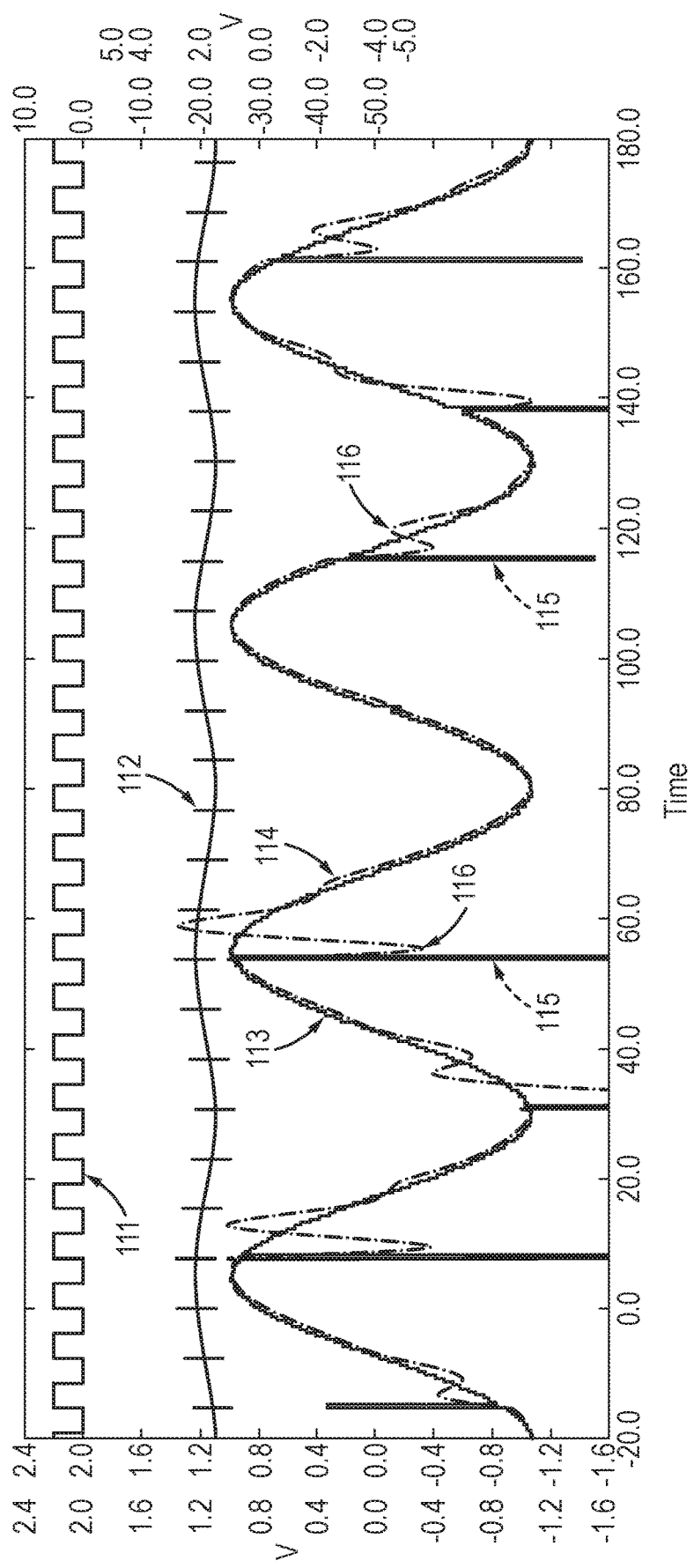
Figure 24:
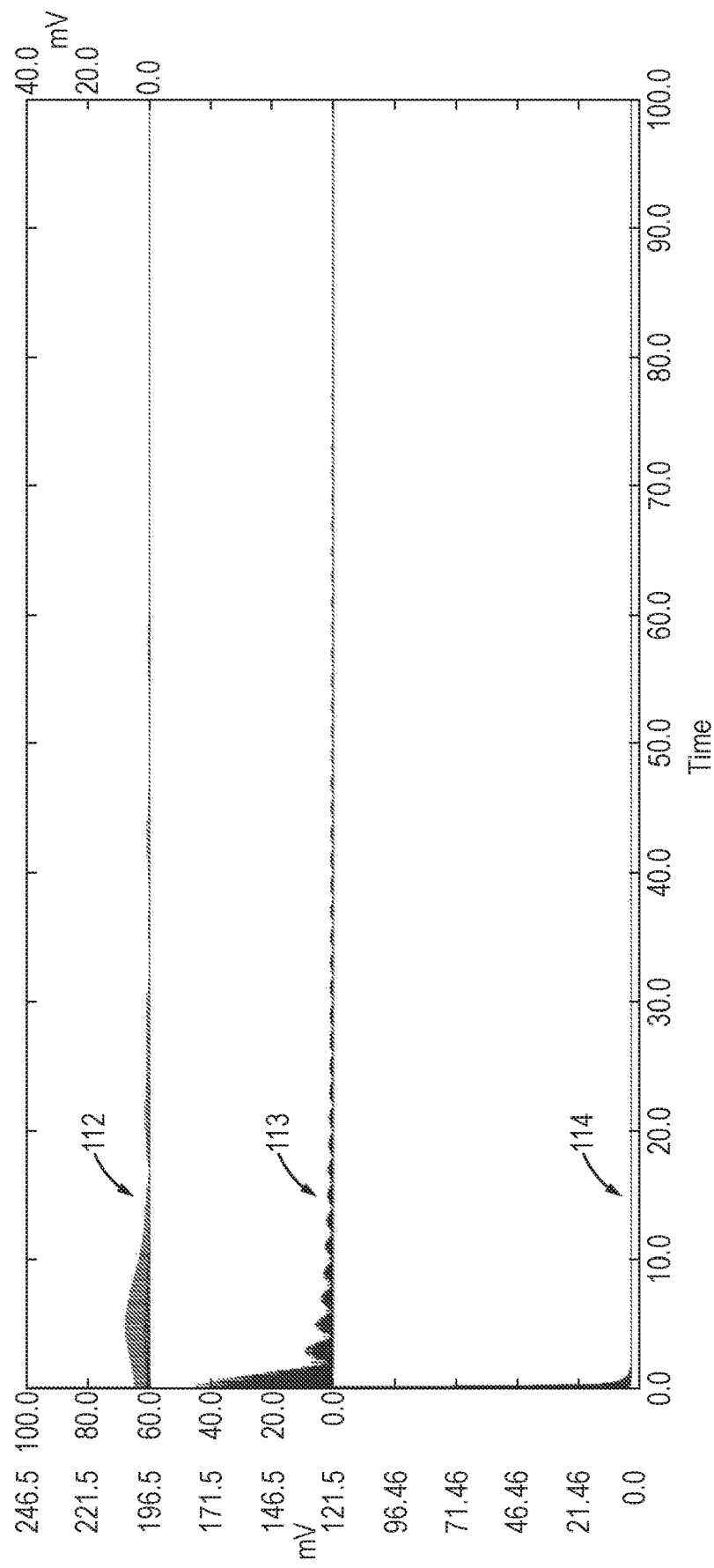
Figure 25:
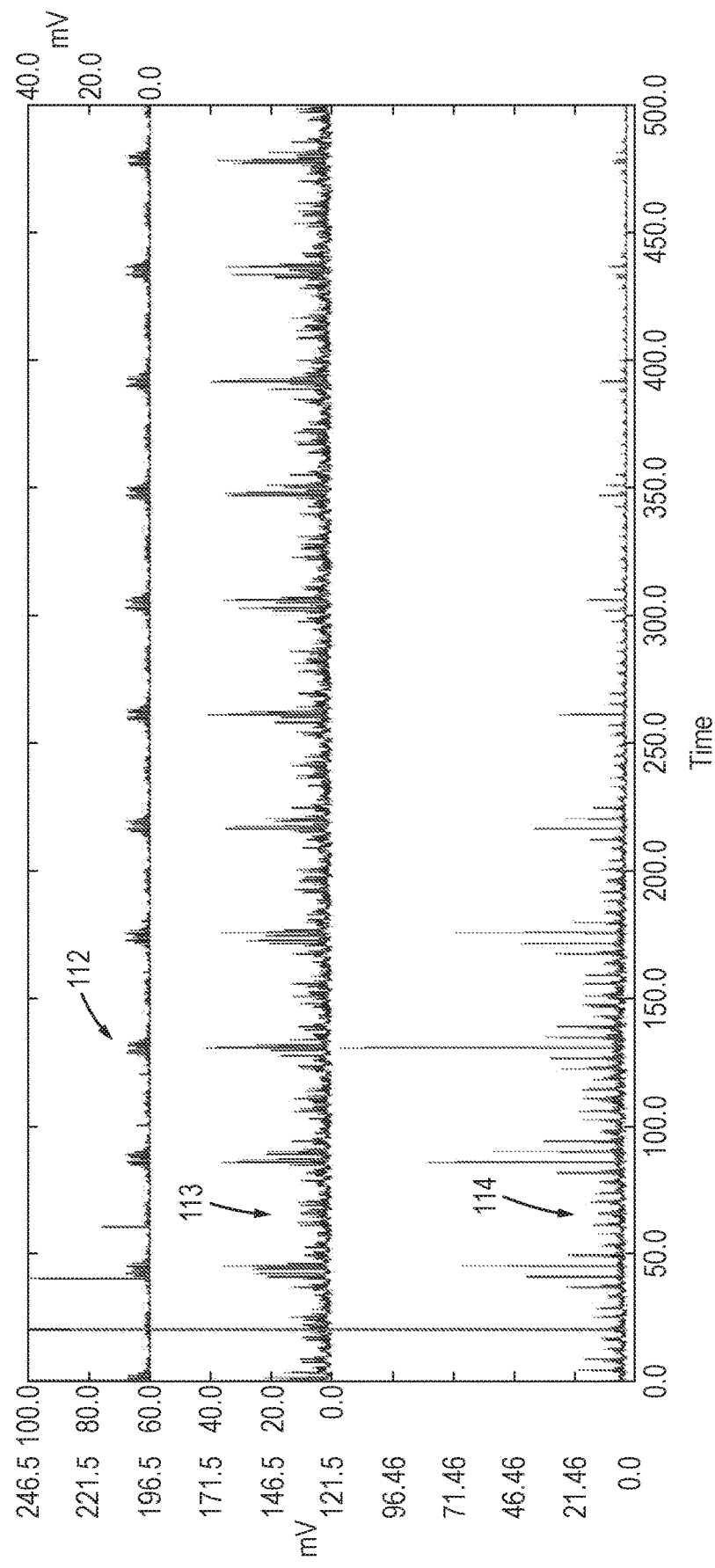

FIG. 23 shows results of a desynchronised case in the temporal domain and FIGS. 24 and 25 show results of the desynchronised case in the frequency domain in a broad frequency band and a low frequency band, respectively. FIGS. 23 to 25 illustrate the desynchronised stimulation clock 111, the analogue input with artefacts 112 to the ADC 26, the discretised input 113 to the ADC 26, and the filtered discretised input 114 to the ADC 26. The desynchronised case represents the situation where the neuromodulation is now turned ON, but the desynchronised stimulation clock 111 was not synchronised with the clock signal of the ADC 26, i.e. the stimulation pulse was present in the analogue input 112 converted by the ADC 26, leading to large artefacts 115 in the discretised input 113. Those large artefacts 115 are caused by sampling the stimulation pulses, providing sharp 'impulses' in the digitised signal.

Those large artefacts 115 in the discretised input 113 induce the (rough) impulse response of the second order low-pass filter providing temporal impulse responses 116 in the filtered discretised input 114. This major effect of the stimulation pulse artefact in the temporal domain has been in the vast majority of cases overlooked, and has not been reported in the scientific literature to the best of the inventors' knowledge. The temporal impulse responses 116 of the filter are not something that cannot be easily seen in the spectrum domain. Since the impulses in the digitised signal cannot be filtered (prior to the filter stage), they will always exert the impulse response of the following digital filter, which will then necessarily lead to erroneous interpretations of the recorded LFP signal in the temporal domain.

In the frequency domain shown in FIGS. 24 and 25, the artefact harmonics of the analogue input 112 aliased in a complex pattern in the discretised input 113 that extends from the low frequency band (below 10 Hz) to beyond 100 kHz as seen in FIG. 24. Most of the aliased harmonics were well suppressed by the second-order low-pass filter, as can bee seen in the filtered discretised input 114 in FIGS. 24 and 25, as we should expect it. However, the aliased harmonics below the cutting frequency of the filter remain intact, and inexorably contaminate the low frequency band of interest (between 1 to 500 Hz, and especially 1 to 100 Hz). Those low frequency band harmonics, several magnitudes larger than the signal of interest, are then impossible to remove, and compromise any further processing.

Figure 26:
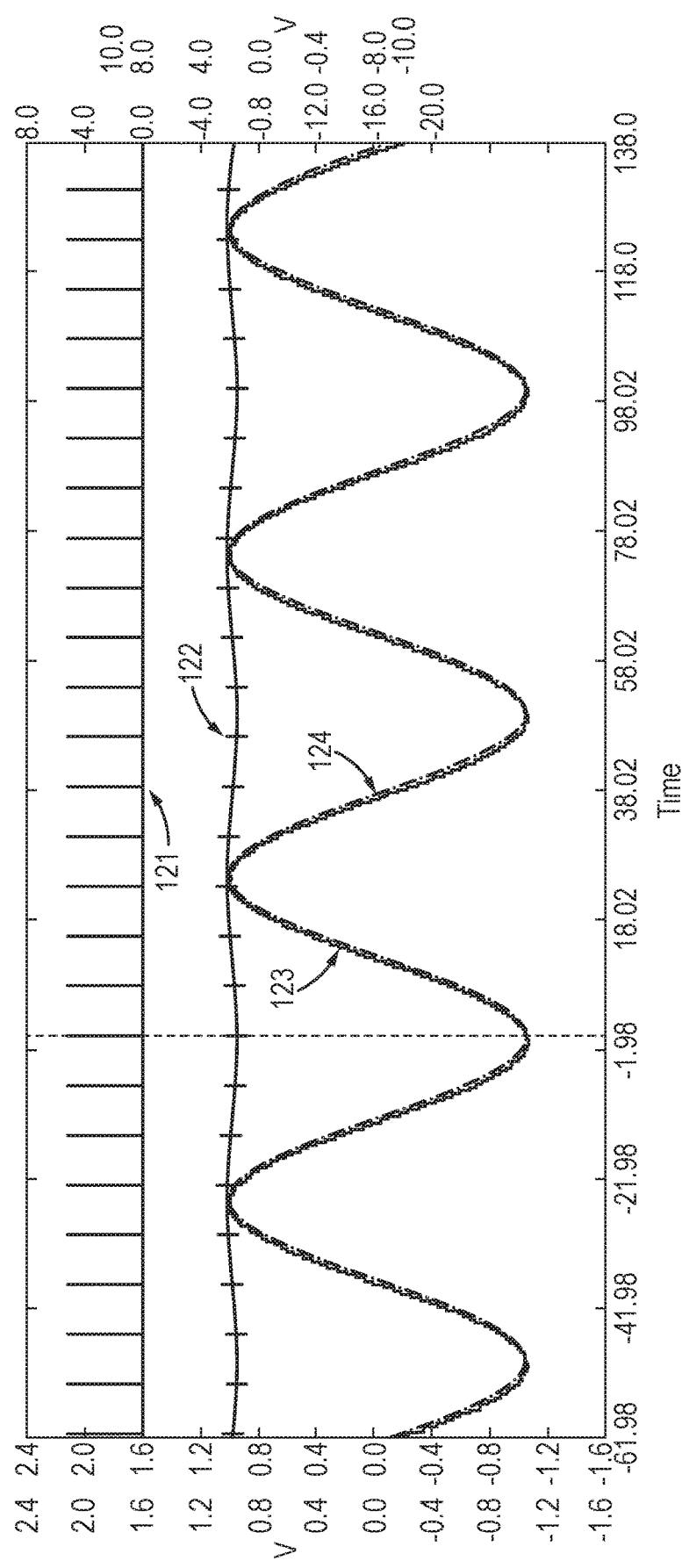
Figure 27:
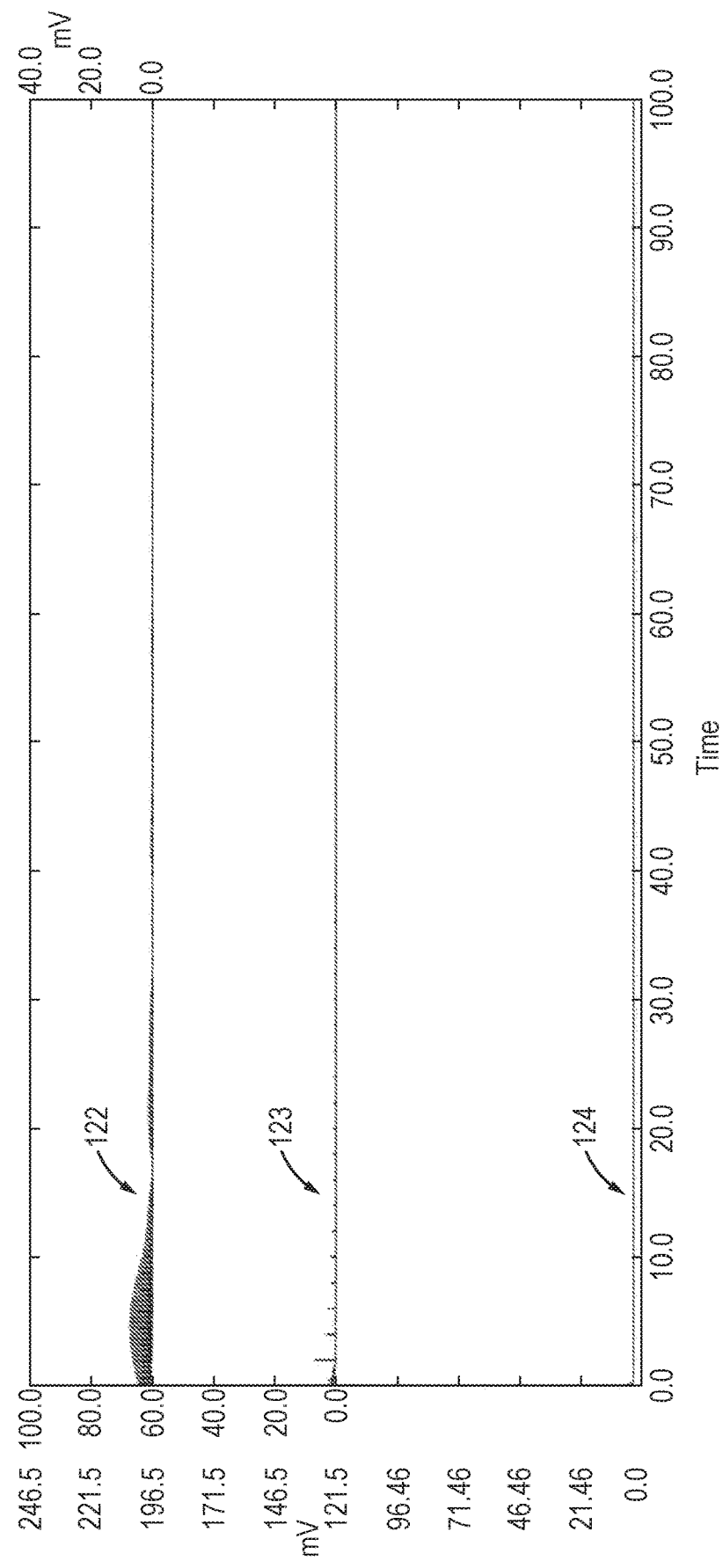
Figure 28:
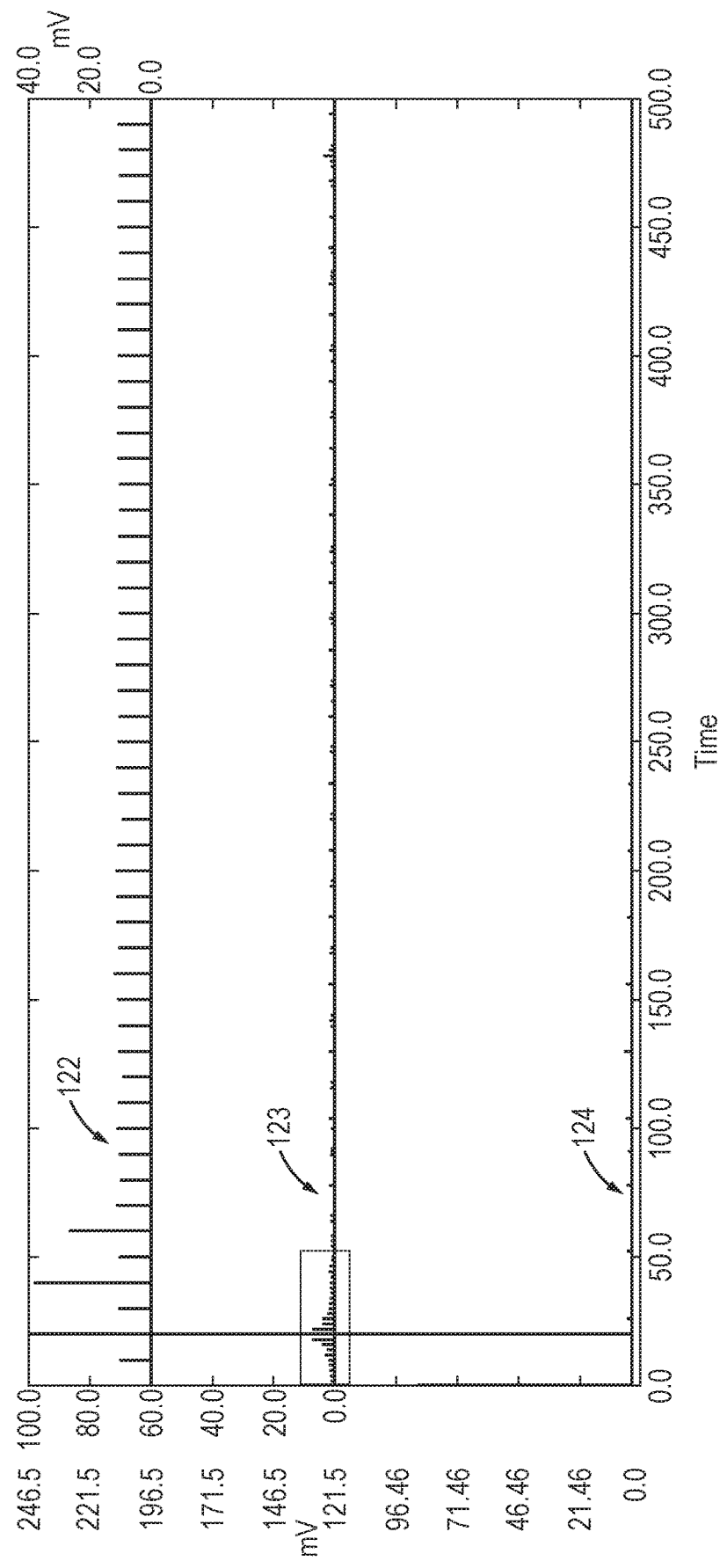

FIG. 26 shows results of a synchronised case in the temporal domain and FIGS. 27 and 28 show results of the synchronised case in the frequency domain in a broad frequency band and a low frequency band, respectively. FIGS. 26 to 27 illustrate the synchronised stimulation clock 121, the analogue input 122 to the ADC 26, the discretised input 123 to the ADC 26, and the filtered discretised input 124 to the ADC 26. The synchronised case represents the situation where the neuromodulation is still turned ON, but the synchronised stimulation clock 121 was synchronised with the clock signal of the ADC 26, i.e. the stimulation pulse was present in the analogue input 122 converted by the ADC 26, but due to the application of the techniques disclosed herein, there were no large artefacts in the discretised input 123 as seen in the desynchronised case mentioned above.

The first striking difference was the total absence of any pulse artefacts in the discretised signal in the synchronised case shown in FIG. 26, in comparison to the desynchronised case shown in FIG. 23.

Also, as shown in FIG. 26, the original sinewave without any filter impulse response is completely in the filtered discretised input 124 in the temporal domain as compared to the desynchronised case shown in FIG. 23. The total absence of the impulse of the filter in the temporal domain is a fundamental characteristic allowing this time to make proper interpretation of the recorded LFP in the temporal domain.

But, the most spectacular result was found in the spectral domain shown in FIG. 27. The same artefact harmonics were present in the analogue input 122 as with the desynchronised case shown in FIG. 24, but they did not alias in a complex pattern in the discretised input 123. Instead, the discretised input 123 had the exact same spectrum of the nominal case without stimulation artefact shown in FIG. 22.

There were not any aliased harmonics in the lower frequency band of interest (between 1 to 500 Hz, and especially 1 to 100 Hz), as shown by the filtered discretised input 124 in FIG. 28. This dramatic change can be compared to the desynchronised case shown in FIG. 25 to fully appreciated the efficacy of the techniques disclosed herein. The only remaining harmonics are those already present in the nominal case due to background noise.

Figure 29:
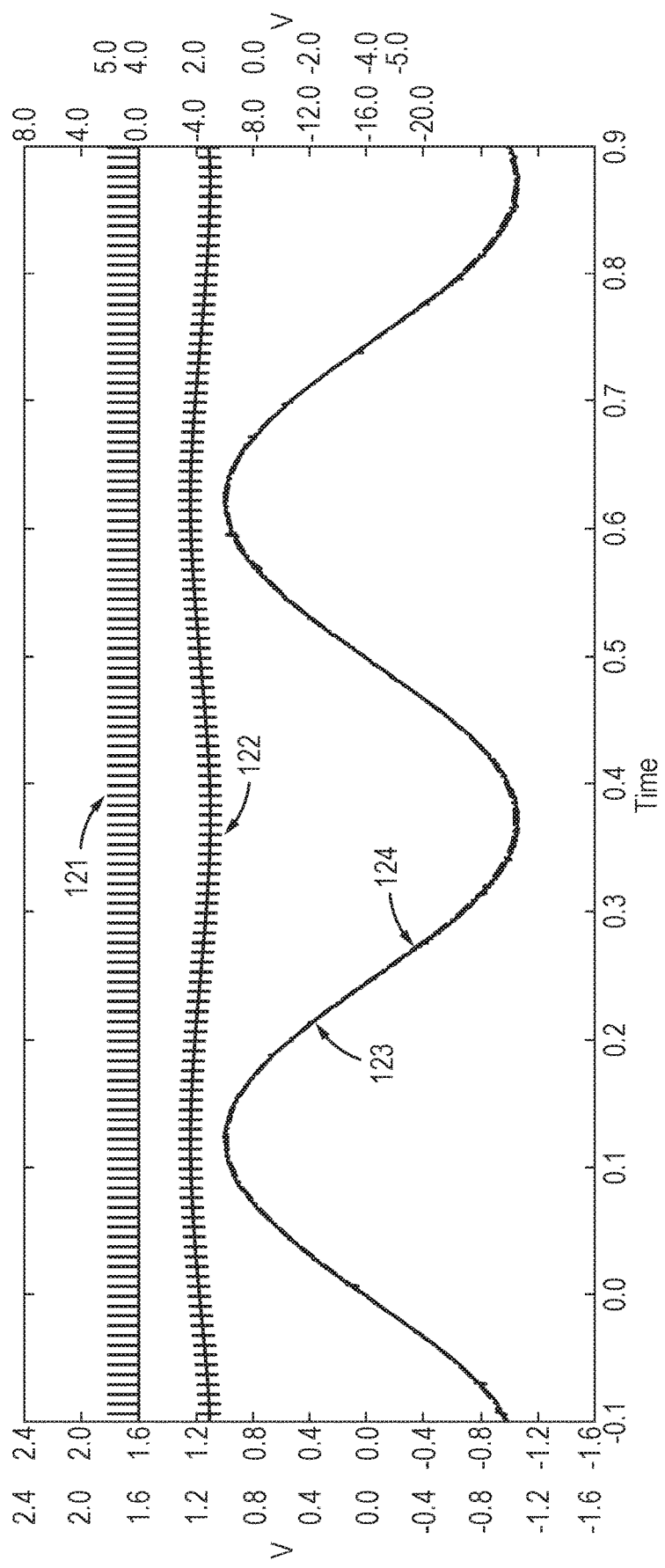
Figure 30:
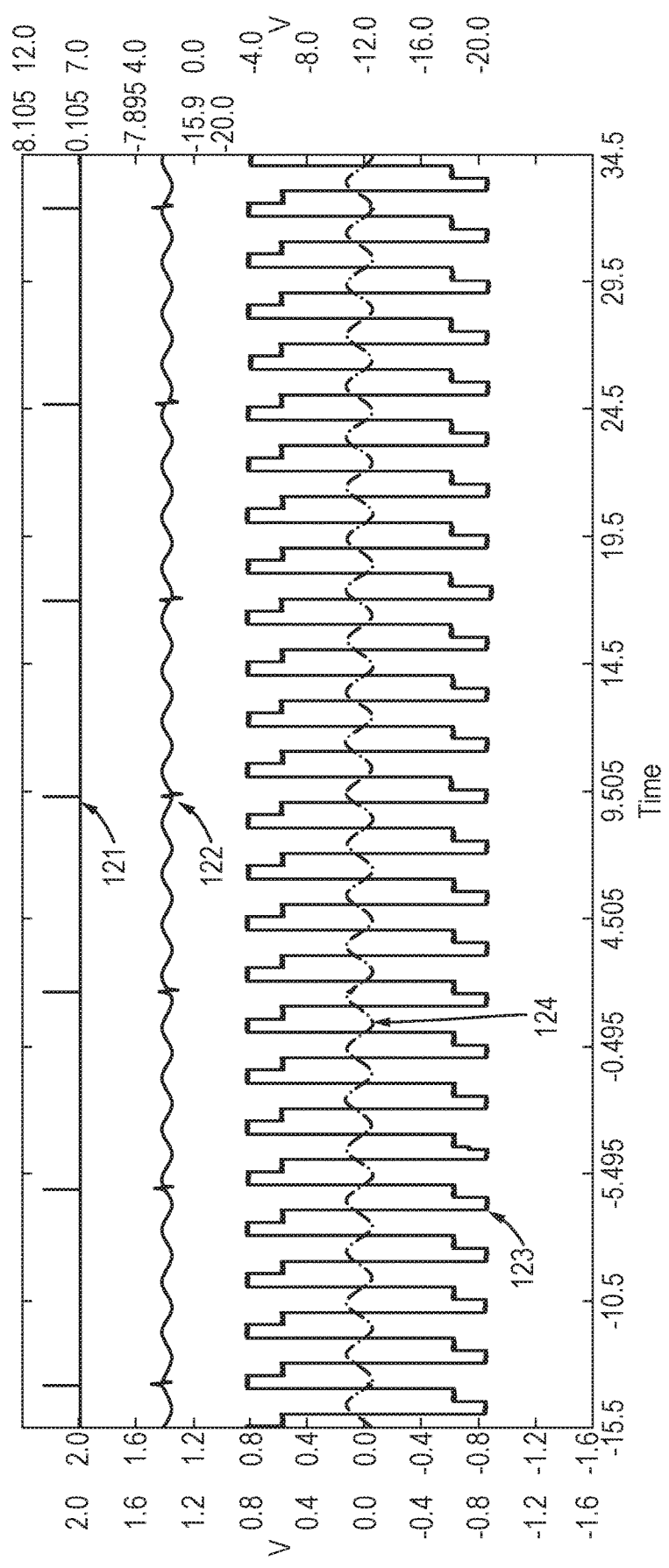
Figure 31:
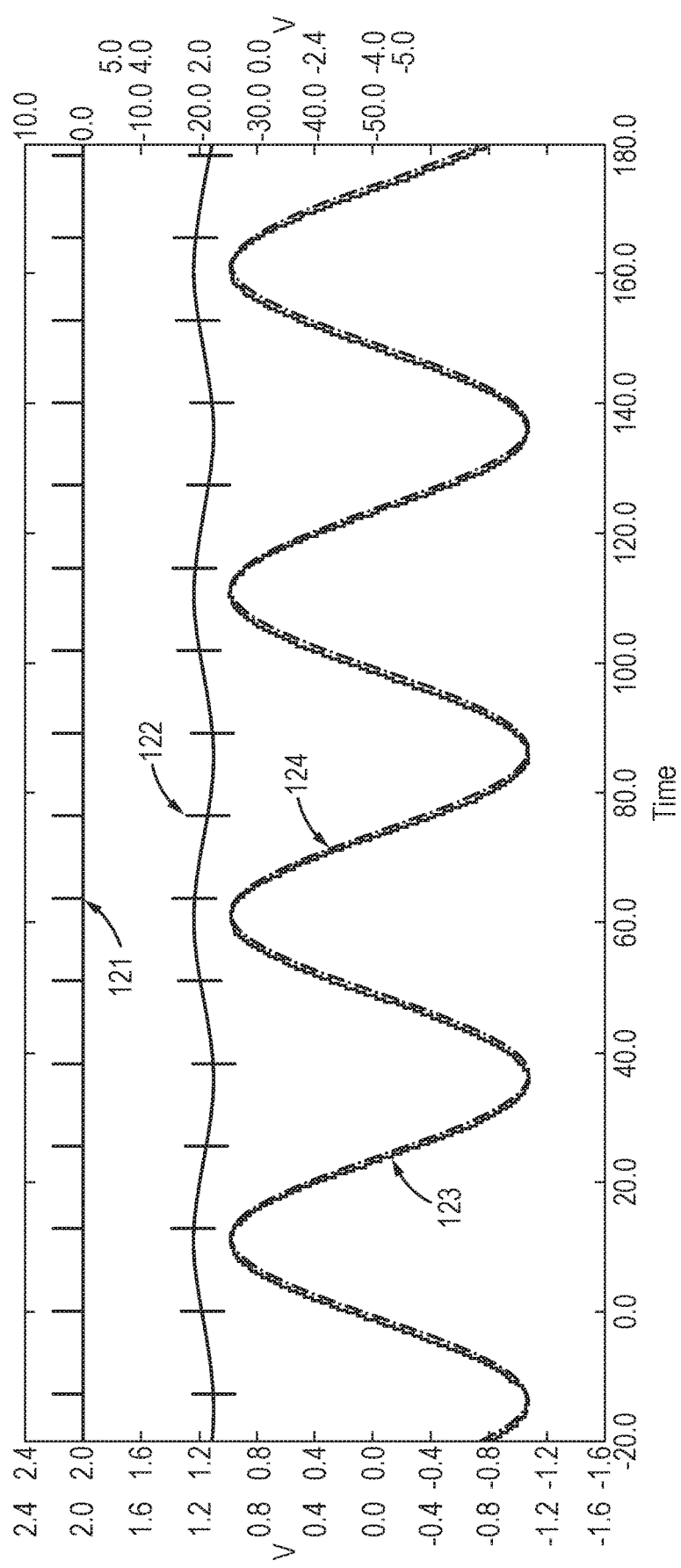
Figure 32:
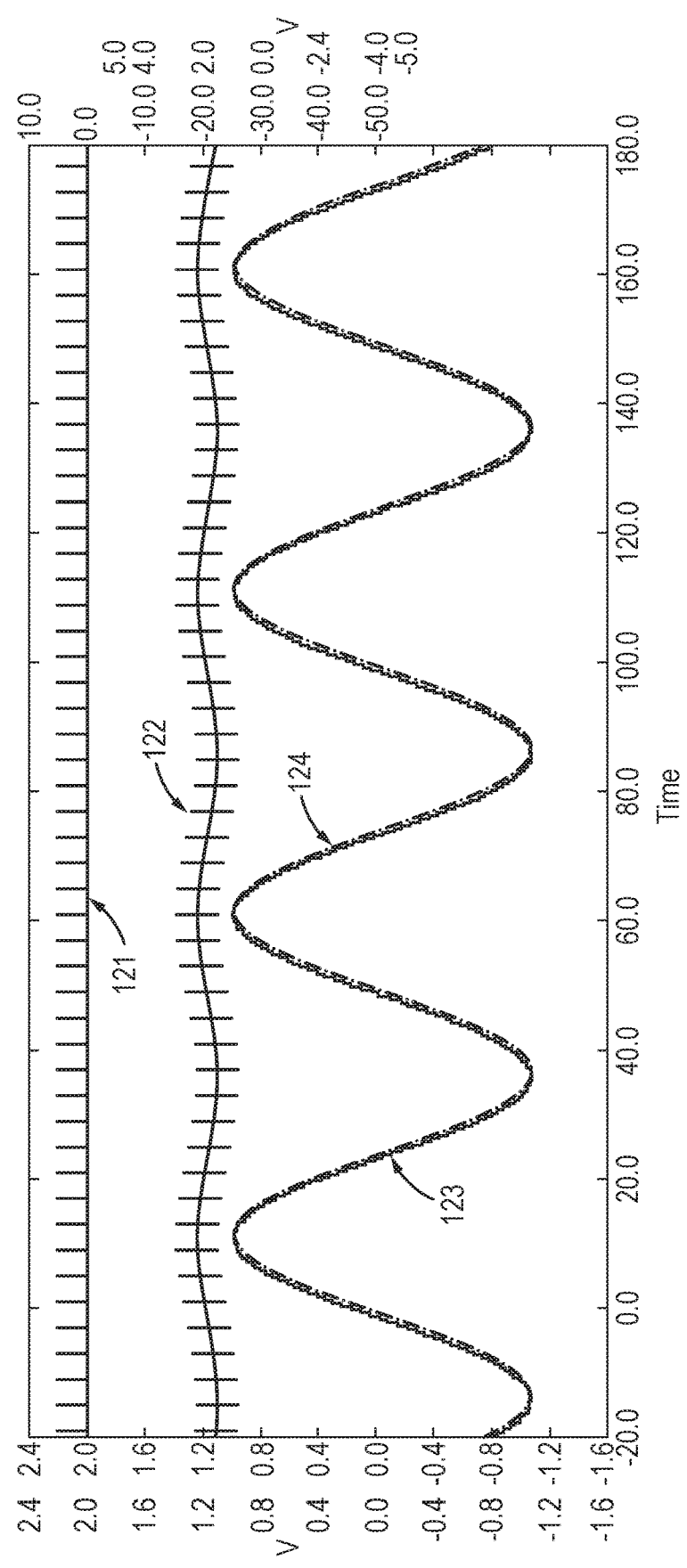

Performance was also tested at a very low frequency of 2 Hz and at a high frequency of 500 Hz, the results of which are shown in FIGS. 29 and 30, respectively. In addition, performance was tested with stimulation frequencies of 78 Hz and 250 Hz, the results of which are shown in FIGS. 31 and 32, respectively. In each case, similar good performance was achieved, thus demonstrating the possibility to change the stimulation frequency in real-time and on-the-fly.

Some modifications that may be applied are as follows.

It is possible to slightly change the synchronisation method to allow for the possibility of a variable stimulation frequency within a given frequency band.

The performance in practical situations may be improved by approaches that reduce the effect of stimulation-induced polarisation of the electrodes 5.

A first approach is to effect synchronisation that ensures that the next sampling time right after the stimulation pulse is carried out after the induced polarisation signal has significantly resumed, noting that the polarisation is a very low transient as compared to the brain signal of interest (essentially an exponential decrease/increase). This may be achieved by reducing the synchronised sampling frequency that is both compatible with sensing the signal of interest (according to the Nyquist-Shannon rules) whilst giving enough time for the induced polarisation signal to resume to an acceptable value, thus avoiding or reducing significantly the step response of the digital filter that might have been exerted otherwise.

A second approach to deal with the electrode polarisation is to use a fast-response non-oscillatory digital filter after the synchronised sensing.

A third approach is to use an active recharge technique based on a biphasic stimulation pulse to dramatically reduce the polarisation induced by stimulation.

These three approaches may optionally be used separately or combined to reduce or avoid the problem of the amplitude step response of the digital filter.

The performance in practical situations may be improved by approaches that reduce the potential saturation of the pre-amplifier 24 due to an overvoltage at its inputs caused by the large stimulation artefacts.

A first approach could be simply based on a classic diode circuit clamping the artefact to a more desirable range. Where precision is a main concern, the classic diode clamping circuits might not be suitable. In such cases, more sophisticated approaches are necessary like using: a blanking of the input of the pre-amplifier 24 by a switched-capacitor but prone to kT/C noise, a signal-line protector (using similar technology as the MAX4505 integrated circuit), or depletion mode FETs (like the approach implemented on the high precision ADA4177 guaranteeing a maximum of 60 μV input offset voltage, 175 nV p-p of voltage noise, and a recovery time of about 10 μs).

While the example above relates to DBS, the method and apparatus may be adapted to other scenarios where closed-loop stimulation of a target area of a human or animal body is performed, including neuroscience applications and more generally bioengineering applications as discussed above. Some specific but non-limitative examples are closed-loop spinal cord stimulation (for example as disclosed in Reference 28), peripheral or autonomic nerve stimulation (for example as disclosed in Reference 29), or closed-loop non-invasive brain stimulation (for example as disclosed in Reference 30). Another example is the emerging domain of sonic neuromodulation, where an ultrasound signal is used to modulate the brain activity. In this example, even if the stimulation modality is ultrasound, it still generates large electrical artefact due the well-established effect of electro-mechanical coupling in neurons. Thus, the method and apparatus may be adapted for in any application where stimulation generates artefacts in the recorded signal, whereas the stimulation and recording modalities do not need to be the same.

Another point should be noted which is related to the actual technology of ADC used. ADC operation consists in principle of two separate processes. The first process is a sample/track-and-hold or more often called a sample-and-hold (S/H) process, the function of which is to maintain the analogue input to be converted relatively constant (usually with a variation less than ½ LSB (least significant bit) of the ADC) during the whole time required to digitise/quantise the input to its equivalent digital value. The second process is the digital quantisation whose type define the structure or technology of the ADC. There are a large number of structures of ADCs that can be broadly classified in five major categories: parallel, segmented, iterative, sigma-delta (often called also delta-sigma) and the remaining types are seen as more 'exotic' or niche ADC.

The conversion time (or settle time) over which sampling occurs is the period over which the sample-and-hold process occurs and depends on the nature of the ADC. The timing at which the conversion time occurs may be controlled, for example by an external sampling clock signal as in the example above, or by a control command if the ADC operates with control data (usually sent via a serial input).

The sample-and-hold circuit and the digital quantisation circuit are often embedded within the same chip in order to improve the digital conversion performances.

It also quite frequent to find ADCs without a sample-and-hold circuit. In such a case, a sample-and-hold circuit may be added before the ADC to define the conversion time to assist in arranging the conversion time outside of the stimulation pulses.

In more sophisticated and high-resolution ADCs (like with the sigma-delta family of ADCs), the sample-and-hold is present but not directly accessible. Instead, a 'Start' conversion pin is usually proposed or a start code to be sent via the serial control input to allow to control the start of the conversion. In that case, these start codes may be used to appropriately implement accordingly this invention. When it is possible to directly access the sample-and-hold circuit control circuit, one can implement directly the proposed patent strategy as described earlier with reference to FIG. 17.

Finally, a last aspect to be taken into consideration is the mode to which data are send by the ADC. In modern high-resolution ADCs (especially for the sigma-delta ADC type), usually two conversion modes can be found (very often to be chosen from the same ADC circuit): a continuous conversion mode where the digital data are 'streamed' continuously and indefinitely after the start conversion signal or command is sent to the ADC, and until a stop signal or command is sent to the ADC. Whereas, in the single-shot mode, a single conversion is performed after the start signal or command, and the ADC waits then the next one in order to perform another conversion. If only the former case is present (continuous conversion mode), an external sample-and-hold circuit may again be added before the ADC in order to define the conversion time over which sampling occurs, for example by maintaining the last analogue value prior to applying the stimulation pulse, and releasing it after a period of time corresponding to the duration of the total stimulation pulse. The latter conversion mode (single-shot mode) is the natural mode for an easy and straightforward implementation of the present methods.

The DBS device 1 has an advantage of scalability. That is, the DBS device 1 can be easily scaled to 1000 or more recording channels by simply using the same synchronisation circuit for all recorders, with almost no further power cost whatsoever. For instance, the DBS device 1 can be scaled efficiently by using a single ADC and by multiplexing its inputs to record from both hemispheres or shared with multiple electrodes.

REFERENCES

Reference 1: Benabid, A. L., Pollak, P., Louveau, A., Henry, S., & Rougemont, J. de, (1987), 'Combined (thalamotomy and stimulation) stereotactic surgery of the vim thalamic nucleus for bilateral parkinson disease', Stereotactic and Functional Neurosurgery, vol. 50, no. 1-6, pp. 344-346

Reference 2: Hariz, M., (2017), 'My 25 stimulating years with dbs in parkinson's disease', Journal of Parkinson's Disease, vol. 7, no. s1, pp. S33-S41

Reference 3: Little, S., Pogosyan, A., Neal, S., Zavala, B., Zrinzo, L., Hariz, M., . . . Brown, P., (2013), 'Adaptive deep brain stimulation in advanced parkinson disease: adaptive dbs in pd', Annals of Neurology, vol. 74, no. 3, pp. 449-457

Reference 4: Little, S., Beudel, M., Zrinzo, L., Foltynie, T., Limousin, P., Hariz, M., . . . Brown, P., (2015), 'Bilateral adaptive deep brain stimulation is effective in parkinson's disease', Journal of Neurology, Neurosurgery & Psychiatry, p. jnnp-2015-310972, Reference 5: TMSi, (2017), Torti 7 user manual (revision 8)', TMSi, User manual 92-0207-0002-0-8

Reference 6: Proakis, J. G. & Manolakis, D. G., (2002), 'Digital signal processing: principles, algorithms and applications'. New Delhi: Prentice-Hall of India.

Reference 7: TMSi, (2018), Torti 7 technical specifications (revision 5)', TMSi, User manual 92-0207-0002-0-8

Reference 8: D'Antona, G. & Ferrero, A., (2006), 'Digital signal processing for measurement systems: theory and applications'. New York, NY: Springer.

Reference 9: Kent, A. R. & Grill, W. M., (2012), 'Recording evoked potentials during deep brain stimulation: development and validation of instrumentation to suppress the stimulus artefact', Journal of Neural Engineering, vol. 9, no. 3, p. 036004

Reference 10: Rossi, L., Foffani, G., Marceglia, S., Bracchi, F., Barbieri, S., & Priori, A., (2007), 'An electronic device for artefact suppression in human local field potential recordings during deep brain stimulation', Journal of Neural Engineering, vol. 4, no. 2, p. 96

Reference 11: Arlotti, M., Rossi, L., Rosa, M., Marceglia, S., & Priori, A., (2016), 'An external portable device for adaptive deep brain stimulation (adbs) clinical research in advanced parkinson's disease', Medical Engineering and Physics, vol. 38, no. 5, pp. 498-505

Reference 12: Arlotti, M., Marceglia, S., Foffani, G., Volkmann, J., Lozano, A. M., Moro, E., Priori, A., (2018), 'Eight-hours adaptive deep brain stimulation in patients with parkinson disease', Neurology Reference 13: Steigerwald et al., 'Pulse duration settings in subthalamic stimulation for parkinson's disease', Movement Disorders, vol. 33, no. 1, pp. 165-169 (2018)

Reference 14: Cagnan, H., Pedrosa, D., Little, S., Pogosyan, A., Cheeran, B., Aziz, T., . . . Brown, P., (2017), 'Stimulating at the right time: phase-specific deep brain stimulation', Brain, vol. 140, no. 1, pp. 132-145

Reference 15: Santillán-Guzmán, A., Heute, U., Muthuraman, M., Stephani, U., & Galka, A., (2013), 'DBS artifact suppression using a time-frequency domain filter', Conference proceedings: . . . Annual International Conference of the IEEE Engineering in Medicine and Biology Society. IEEE Engineering in Medicine and Biology Society. Annual Conference, vol. 2013, pp. 4815-4818

Reference 16: Stanslaski, S., Afshar, P., Cong, P., Giftakis, J., Stypulkowski, P., Carlson, D., . . . Denison, T., (2012), 'Design and validation of a fully implantable, chronic, closed-loop neuromodulation device with concurrent sensing and stimulation', IEEE Transactions on Neural Systems and Rehabilitation Engineering, vol. 20, no. 4, pp. 410-421

Reference 17: Zbrzeski, A., Lewis, N., Rummens, F., Jung, R., N'Kaoua, G., Benazzouz, A., & Renaud, S., (2013), 'Low-gain, low-noise integrated neuronal amplifier for implantable artifact-reduction recording system', Journal of Low Power Electronics and Applications, vol. 3, no. 3, pp. 279-299, Web: http://www.mdpi.com/2079-9268/3/3/279

Reference 18: Hashimoto, T., Elder, C. M., & Vitek, J. L., (2002), 'A template subtraction method for stimulus artifact removal in high-frequency deep brain stimulation', Journal of Neuroscience Methods, vol. 113, no. 2, pp. 181-186.
Reference 19: Wagenaar, D. A. & Potter, S. M., (2002), 'Real-time multi-channel stimulus artifact suppression by local curve fitting', Journal of Neuroscience Methods, vol. 120, no. 2, pp. 113-120.
Reference 20: Al-ani, T., Cazettes, F., Palfi, S., & Lefaucheur, J.-P., (2011), 'Automatic removal of high-amplitude stimulus artefact from neuronal signal recorded in the subthalamic nucleus', Journal of Neuroscience Methods, vol. 198, no. 1, pp. 135-146.
Reference 21: Sun, Y., Farzan, F., Garcia Dominguez, L., Barr, M. S., Giacobbe, P., Lozano, A. M., . . . Daskalakis, Z. J., (2014), 'A novel method for removal of deep brain stimulation artifact from electroencephalography', Journal of Neuroscience Methods, vol. 237, pp. 33-40.
Reference 22: Qian, X., Chen, Y., Feng, Y., Ma, B., Hao, H., & Li, L., (2017), 'A method for removal of deep brain stimulation artifact from local field potentials', IEEE transactions on neural systems and rehabilitation engineering: a publication of the IEEE Engineering in Medicine and Biology Society, vol. 25, no. 12, pp. 2217-2226.
Reference 23: Blum, R. A., Ross, J. D., Brown, E. A., & DeWeerth, S. P., (2007), 'An integrated system for simultaneous, multichannel neuronal stimulation and recording', IEEE Transactions on Circuits and Systems I: Regular Papers, vol. 54, no. 12, pp. 2608-2618
Reference 24: Brown, E. A., Ross, J. D., Blum, R. A., Nam, Y., Wheeler, B. C., & DeWeerth, S. P., (2008), 'Stimulus-artifact elimination in a multi-electrode system', IEEE Transactions on Biomedical Circuits and Systems, vol. 2, no. 1, pp. 10-21
Reference 25: Rolston, J. D., (2009), 'A low-cost multielectrode system for data acquisition enabling real-time closed-loop processing with rapid recovery from stimulation artifacts', Frontiers in Neuroengineering, vol. 2, Web: http://journal.frontiersin.org/article/10.3389/neuro.16.012.2009/abstract
Reference 26: Rolston, J. D., Gross, R. E., & Potter, S. M., (September 2009), 'NeuroRighter: closed-loop multielectrode stimulation and recording for freely moving animals and cell cultures', pp. 6489-6492
Reference 27: Unser, M., (2000), 'Sampling-50 years after shannon', Proceedings of the IEEE, vol. 88, no. 4, pp. 569-587
Reference 28: Russo et al., 'Effective Relief of Pain and Associated Symptoms With Closed-Loop Spinal Cord Stimulation System: Preliminary Results of the Avalon Study', Neuromodulation. 2018 January; 21(1):38-47. doi: 10.1111/ner.12684. Epub 2017 Sep. 18
Reference 29: Kobayashi et al., 'Cardiac Autonomic Nerve Stimulation in the Treatment of Heart Failure', Ann Thorac Surg. 2013 July; 96(1): 339-345
Reference 30: Zrenner et al., 'Closed-Loop Neuroscience and Non-Invasive Brain Stimulation: A Tale of Two Loops', Front Cell Neurosci. 2016; 10: 92
Reference 31: Lio, G., Thobois, S., Ballanger, B., Lau, B., & Boulinguez, P., (2018), 'Removing deep brain stimulation artifacts from the electroencephalogram: issues, recommendations and an open-source toolbox', Clinical Neurophysiology, vol. 129, no. 10, pp. 2170-2185

The invention claimed is:

1. A method of simultaneously generating a stimulation signal comprising stimulation pulses for stimulating a target area of a human or animal body and sampling an electrophysiological signal measured from the body for deriving a feedback signal for closed-loop control of the stimulation signal, by an analogue to digital converter at a sampling frequency of the analogue to digital converter,
wherein the sampling frequency of the analogue to digital converter is a positive integer value times a stimulation frequency at which the simulation pulses are generated, and the generation of the stimulation signal and the sampling of the electrophysiological signal by the analogue-to-digital converter at the sampling frequency of the analogue to digital converter are synchronised and have a relative phase selected to cause the sampling by the analogue to digital converter to occur outside the stimulation pulses.

2. A method according to claim 1, wherein the positive integer value is a plural integer value.

3. A method according to claim 2, wherein the plural integer value is at least four.

4. A method according to claim 1, wherein the method comprises:
generating a master clock signal;
deriving a sampling clock signal and a stimulation clock signal synchronously from the master clock signal with a relative delay introduced between the sampling clock signal and the stimulation clock signal to adjust their relative phase;
the sampling being performed at timings controlled by the sampling clock signal and the generation of the stimulation signal being performed at timings controlled by the stimulation clock signal.

5. A method according to claim 4, wherein the sampling clock signal is the master clock signal.

6. A method according to claim 4, wherein the stimulation clock signal is derived by frequency dividing the master clock signal by a plural integer value.

7. A method according to claim 4, wherein the relative delay is introduced between the sampling clock signal and the stimulation clock signal by delaying the stimulation clock signal before or after frequency dividing the master clock signal by the plural integer value.

8. A method according to claim 4, wherein the relative delay is introduced between the sampling clock signal and the stimulation clock signal by delaying the sampling clock signal.

9. A method according to claim 1, further comprising deriving a local field potential signal from the electrophysiological signal after said analogue-to-digital conversion and controlling the generation of the stimulation signal on the basis of the local field potential signal.

10. A method according to claim 1, further comprising deriving a feedback signal from the sampled electrophysiological signal, and performing closed-loop control of the stimulation signal on the basis of the feedback signal.

11. A method according to claim 1, wherein the target area is a target area in the nervous system of the human or animal body.

12. A method according to claim 1, further comprising measuring the electrophysiological signal.

13. A method according to claim 1, further comprising applying the stimulation signal to the target area.

14. A stimulation device comprising:
a stimulation generator arranged to generate a stimulation signal comprising stimulation pulses for stimulation of a target area of a human or animal body; and
an analogue-to-digital converter arranged to sample an electrophysiological signal measured from the body at a sampling frequency of the analogue to digital converter to generate a digital electrophysiological signal for deriving a feedback signal for closed-loop control of the stimulation signal, wherein the sampling frequency of the analogue-to-digital converter is a positive integer value times a stimulation frequency at which the stimulation generator is arranged to generate the simulation pulses, and the device is arranged so that the generation of stimulation signal and the sampling of the electrophysiological signal by the analogue-to-digital converter at the sampling frequency of the analogue to digital converter are synchronised and have a relative phase selected to cause the sampling by the analogue to digital converter to occur outside the stimulation pulses.

15. A stimulation device according to claim 14, wherein the positive integer value is a plural integer value.

16. A stimulation device according to claim 15, wherein the plural integer value is at least four.

17. A stimulation device according to claim 14, wherein the device comprises:

a master clock arranged to generate a master clock signal; and a clock signal unit arranged to derive a sampling clock signal and a stimulation clock signal synchronously from the master clock signal with a relative delay introduced between the sampling clock signal and the stimulation clock signal to adjust their relative phase, the circuitry supplying the sampling clock signal to the analogue-to-digital converter and supplying the stimulation clock signal to the stimulation generator, wherein the analogue-to-digital converter is arranged to perform the sampling at timings controlled by the sampling clock signal, and the stimulation generator is arranged to generate the stimulation pulses at timings controlled by the stimulation clock signal.

18. A stimulation device according to claim 15, wherein the sampling clock signal is the master clock signal.

19. A stimulation device according to claim 18, wherein the clock signal unit is arranged to derive the stimulation clock signal by frequency dividing the master clock signal by a plural integer value.

20. A stimulation device according to claim 18, wherein the clock signal unit is arranged to introduce the relative delay between the sampling clock signal and the stimulation clock signal by delaying the stimulation clock signal after frequency dividing the master clock signal by the plural integer value.

21. A stimulation device according to claim 18, wherein the clock signal unit is arranged to introduce the relative delay between the sampling clock signal and the stimulation clock signal by delaying the sampling clock signal.

22. A stimulation device according to claim 14, further comprising a processing circuit arranged to derive a feedback signal from the digital electrophysiological signal and a closed-loop control circuit arranged to control the operation of the stimulation generator on the basis of the feedback signal.

23. A stimulation device according to claim 14, further comprising electrodes supplied with the stimulation signal and from which the electrophysiological signal is supplied.

* * * * *